(12) United States Patent
Romano et al.

(10) Patent No.: US 9,234,231 B2
(45) Date of Patent: Jan. 12, 2016

(54) SCREENING TOOL FOR ANTI-INFLAMMATORY DRUG DISCOVERY COMPRISING THE FPR2/ALX GENE PROMOTER

(71) Applicant: Università degli Studi "G. D'Annunzio" Chieti-Pescara, Chieti Scalo (CH) (IT)

(72) Inventors: Mario Romano, Chieti Scalo (IT); Bartolo Favaloro, Chieti Scalo (IT)

(73) Assignee: UNIVERSITÀ DEGLI STUDI "G. D'ANNUNZIO" CHIETI-PESCARA, Chieti Scalo (CH) (IT)

( * ) Notice: Subject to any disclaimer, the term of this patent is extended or adjusted under 35 U.S.C. 154(b) by 0 days.

(21) Appl. No.: 13/681,496

(22) Filed: Nov. 20, 2012

(65) Prior Publication Data

US 2013/0130269 A1    May 23, 2013

(30) Foreign Application Priority Data

Nov. 23, 2011   (EP) .................................... 11425283

(51) Int. Cl.
   C12Q 1/68      (2006.01)
   C12N 15/00     (2006.01)
   C07H 21/02     (2006.01)
   C07H 21/04     (2006.01)

(52) U.S. Cl.
   CPC ............... *C12Q 1/68* (2013.01); *C12Q 1/6883* (2013.01); *C12Q 2600/136* (2013.01); *C12Q 2600/156* (2013.01)

(58) Field of Classification Search
   None
   See application file for complete search history.

(56) References Cited

U.S. PATENT DOCUMENTS

| 6,245,512 | B1 | 6/2001 | Williams et al. |
| 2002/0052529 | A1 | 5/2002 | Kase et al. |

FOREIGN PATENT DOCUMENTS

| KR | 20110117944 | 10/2011 |
| WO | 0220759 A2 | 3/2002 |
| WO | 2005047899 A2 | 5/2005 |
| WO | 2008073303 A2 | 6/2008 |

OTHER PUBLICATIONS

Haviland et al., "Structure, 5'-Flanking Sequence, and Chromosome Location of the Human N-Formyl Peptide Receptor Gene. A Single-Copy Gene Comprised of Two Exons on Chromosome 19q.13.3 That Yields Two Distinct Transcripts by Alternative Polyadenylation" 32 Biochemistry 4168-4174 (1993).*
Wan et al., "Leukotriene B4/antimicrobial peptide LL_37 proinflammatory circuits are mediated by BLT1 and FPR2/ALX and are counterregulated by lipoxin A4 and resolvin El" 25 The FASEB Journal 1697-1705 (May 2011).*
Perez et al. "Cloning of the Gene Coding for a Human Receptor for Formyl Peptides. Characterization of a Promoter Region and Evidence for Polymorphic Expression" 31 Biochemistry 11595-11599 (1992).*
Machine Translation of Korean Patent No. 10-2011-0117944 (Oct. 28, 2011).*
Gwinn et al. "Single Nucleotide Polymorphisms of the N-Formyl Peptide Receptor in Localized Juvenile Periodontitis" 70(1) Journal of Periodontology 1194-1201 (1999).*
Giacomini et al., "The Pharmacogenetics Research Network: From SNP Discovery to Clinical Drug Response" 81(3) Nature Clinical Pharmacology and Therapeutics 328-345 (2007).*
Robert et al., "Predicting drug response and toxicity based on gene polymorphisms" 54 Clinical Reviews in Oncology/Hematology 171-196 (2005).*
Extended European Search Report dated Mar. 27, 2012 in related application 11425283.6.
Kimura, Kouichi et al. "Diversification of transcriptional modulation: large-scale identification and characterization of putative alternative promoters of human genes," Genome Research, Cold Spring Harbor Lab., vol. 16, No. 1, Jan. 1, 2006, pp. 55-65.
P. Maderna et al., "FPR2/ALX receptor expression and internalization are critical for lipoxin A4 and annexin-derived peptide-stimulated phagocytosis", The FASEB Journal, vol. 24, No. 11, Nov. 1, 2010, pp. 4240-4249.
Forsman H, et al., "Stable formyl peptide receptor agonists that activate the neutrophil NADPH-oxidase identified through screening of a compound library," Biochemical Pharmacology, vol. 81, No. 3, Feb. 1, 2011, p. 402-411.
Dufton N et al., "Therapeutic anti-inflammatory potential of formyl-peptide receptor agonists", Pharmacology and Therapeutics, vol. 127, No. 2, Aug. 1, 2010, pp. 175-188.
Murphy et al., "A structural homologue of the N-formyl peptide receptor," J. of Biological Chemicstry, vol. 267, No. 11, pp. 7637-7643, 1992.
Sawmynaden et al., "Glucocorticoid upregulation of the annexin-A1 receptor in leukocytes", Biochemical and Biophysical Research Communications 349 (2006), 1351-1355.
Gronert et al., "Identification of a Human Enterocyte Lipoxin A4 Receptor That is Regulated by Interleukin (IL)-13 and Interferon gamma and Inhibits Tumor Necrosis Factor alpha-induced IL-8 Release," J. Exp. Med., vol. 187, No. 8, Apr. 20, 1998, 1285-1294.

* cited by examiner

*Primary Examiner* — Nancy J Leith
(74) *Attorney, Agent, or Firm* — Kristina Castellano; Castellano PLLC

(57) ABSTRACT

A screening tool for anti-inflammatory drug discovery and for the detection of the risk or presence of inflammatory conditions, comprising the sequence of the FPR2/ALX gene promoter, is disclosed.

3 Claims, 11 Drawing Sheets

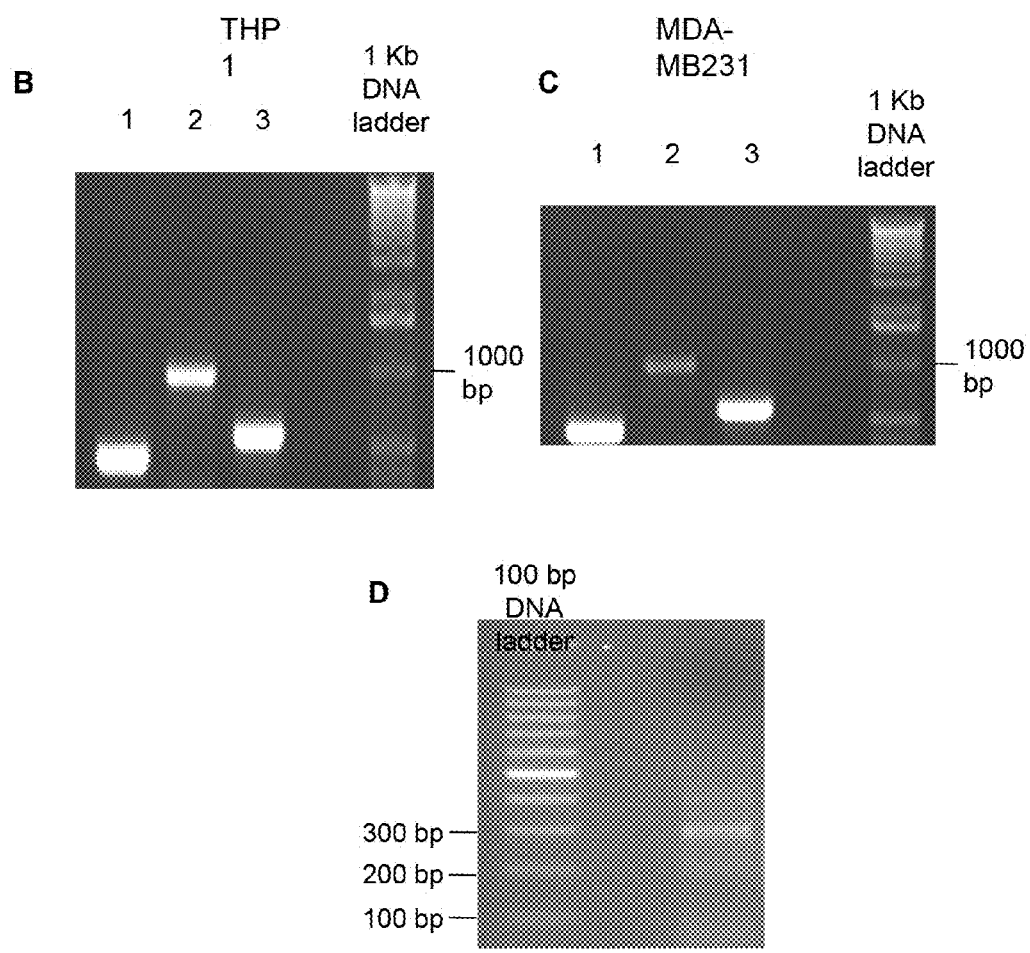
Figure 1 B-D

SCREENING TOOL FOR ANTI-INFLAMMATORY DRUG DISCOVERY COMPRISING THE FPR2/ALX GENE PROMOTER

CLAIM FOR PRIORITY

This application claims priority to European Patent Application No. 11425283.6 filed on Nov. 23, 2011, the contents of which are incorporated herein by reference.

TECHNICAL FIELD

The present invention refers to the field of pharmaceuticals and diagnostics, in particular to a screening tool for anti-inflammatory drug discovery and for the detection of the risk or presence of inflammatory conditions. The screening tool comprises the sequence of the FPR2/ALX gene promoter.

BACKGROUND OF THE INVENTION

Resolution of inflammation, an active process that prevents damage to the host and re-establishes homeostasis, is governed by specific mediators (Serhan, C. N., S. D. Brain, C. D. Buckley, D. W. Gilroy, C. Haslett, L. A. O'Neill, M. Perretti, A. G. Rossi, and J. L. Wallace. 2007. Resolution of inflammation: state of the art, definitions and terms. FASEB J 21:325-332). Among these, the arachidonic acid (AA)-derived lipoxins (LX), an acronym for lipoxygenase (LO)-interaction-products, were the first autacoids recognized to carry dual antiinflammatory and pro-resolution activities (Maderna, P., and C. Godson. 2009. Lipoxins: resolutionary road. Br J Pharmacol 158:947-959; Serhan, C. N., M. Hamberg, and B. Samuelsson. 1984a. Lipoxins: novel series of biologically active compounds formed from arachidonic acid in human leukocytes. Proc Natl Acad Sci USA 81:5335-5339; Serhan, C. N., M. Hamberg, and B. Samuelsson. 1984b. Trihydroxytetraenes: a novel series of compounds formed from arachidonic acid in human leukocytes. Biochem Biophys Res Commun 118:943-949). LXA4 (5,6,15S-trihydroxy-7,9,11,13-trans-1'-cis-eicosatetraenoic acid) is biosynthesized during cell-cell interactions by transcellular metabolic routes involving 5-LO and 12- or 15-LO (Maderna, P., and C. Godson. 2009. Lipoxins: resolutionary road. Br J Pharmacol 158:947-959; Romano, M. 2010. Lipoxin and aspirin-triggered lipoxins. ScientificWorldJournal 10:1048-1064). Within the vasculature, different pathways lead to the biosynthesis of LX. During platelet-leukocyte interactions, leukotriene (LT) A4 released from leukocytes is converted into LXA4 and B4 by platelet 12-LO (Romano, M., and C. N. Serhan. 1992. Lipoxin generation by permeabilized human platelets. Biochemistry 31:8269-8277; Romano, M., X. S. Chen, Y. Takahashi, S. Yamamoto, C. D. Funk, and C. N. Serhan. 1993. Lipoxin synthase activity of human platelet 12-lipoxygenase. Biochem J 296 (Pt 1):127-133). In addition, aspirin, a widely used anti-inflammatory and anti-thrombotic drug, promotes the biosynthesis of 015 epimers of LX (5,6,15R-trihydroxy-7,9,11,13-trans-11-cis-eicosatetraenoic acid), also termed "aspirin triggered" LX (ATL) via acetylation of endothelial cyclooxygenase-2 (COX-2) (Claria, J., and C. N. Serhan. 1995. Aspirin triggers previously undescribed bioactive eicosanoids by human endothelial cell-leukocyte interactions. Proc Natl Acad Sci USA 92:9475-9479). ATL proved to mediate the anti-inflammatory actions of low-dose aspirin in humans, independently from inhibition of prostanoid biosynthesis (Morris, T., M. Stables, A. Hobbs, P. de Souza, P. Colville-Nash, T. Warner, J. Newson, G. Bellingan, and D. W. Gilroy. 2009. Effects of low-dose aspirin on acute inflammatory responses in humans. J Immunol 183:2089-2096). Importantly, statins, through the S-nitrosilation of COX-2, also trigger the generation of 15-epi-LXA4 (Birnbaum, Y., Y. Ye, Y. Lin, S. Y. Freeberg, S. P. Nishi, J. D. Martinez, M. H. Huang, B. F. Uretsky, and J. R. Perez-Polo. 2006. Augmentation of myocardial production of 15-epi-lipoxin-a4 by pioglitazone and atorvastatin in the rat. Circulation 114:929-935; Planaguma, A., M. A. Pfeffer, G. Rubin, R. Croze, M. Uddin, C. N. Serhan, and B. D. Levy. 2010. Lovastatin decreases acute mucosal inflammation via 15-epi-lipoxin A4. Mucosal Immunol 3:270-279). LXA4 and ATL modulate the immune-inflammatory response by inhibiting polymorphonuclear leukocyte (PMN) infiltration in inflamed tissues and stimulating phagocytosis of apoptotic PMN and microbes (Maderna, P., and C. Godson. 2009. Lipoxins: resolutionary road. Br J Pharmacol 158:947-959) in vivo, thus promoting resolution. Moreover, they display potent protective actions in the cardiovascular district, by directly stimulating the production of prostacyclin and nitric oxide, upregulating heme oxygenase-1, and reducing oxidative stress in endothelial cells (Maderna, P., and C. Godson. 2009. Lipoxins: resolutionary road. Br J Pharmacol 158:947-959).

LXA4 and ATL exert their bioactions by activating a specific G-protein-coupled receptor (GPCR). Initially reported as a structural homologue of the N-formyl peptide receptor and termed formyl peptide receptor like-1 (FPRL1) (Murphy, P. M., T. Ozcelik, R. T. Kenney, H. L. Tiffany, D. McDermott, and U. Francke. 1992. A structural homologue of the N-formyl peptide receptor. Characterization and chromosome mapping of a peptide chemoattractant receptor family. J Biol Chem 267:7637-7643; Perez, H. D., R. Holmes, E. Kelly, J. McClary, and W. H. Andrews. 1992. Cloning of a cDNA encoding a receptor related to the formyl peptide receptor of human neutrophils. Gene 118:303-304; Ye, R. D., S. L. Cavanagh, O. Quehenberger, E. R. Prossnitz, and C. G. Cochrane. 1992. Isolation of a cDNA that encodes a novel granulocyte N-formyl peptide receptor. Biochem Biophys Res Commun 184:582-589) it was later identified as the LXA4 receptor in human leukocytes (Fiore, S., J. F. Maddox, H. D. Perez, and C. N. Serhan. 1994. Identification of a human cDNA encoding a functional high affinity lipoxin A4 receptor. J Exp Med 180:253-260). The most recent nomenclature has renamed this receptor FPR2/ALX in light of its high affinity for LXA4 (Ye, R. D., F. Boulay, J. M. Wang, C. Dahlgren, C. Gerard, M. Parmentier, C. N. Serhan, and P. M. Murphy. 2009. International Union of Basic and Clinical Pharmacology. LXXIII. Nomenclature for the formyl peptide receptor (FPR) family. Pharmacol Rev 61:119-161). The FPR2/ALX gene (Bao, L., N. P. Gerard, R. L. Jr Eddy, T. B. Shows, and C. Gerard. 1992. Mapping of genes for the human C5a receptor (CSAR), human FMLP receptor (FPR), and two FMLP receptor homologue orphan receptors (FPRH1, FPRH2) to chromosome 19. Genomics 13:437-440) is located on chromosome 19. It spans 9.6 kb and encompasses two exons and two introns. Alternative splicing produces four different transcripts, which encode the same seven transmembrane domain protein of 351 aminoacids. Human FPR2/ALX is highly expressed in myeloid cells and at a lower extent in lymphocytes, endothelial and epithelial cells (Romano, M., I. Recchia, and A. Recchiuti. 2007. Lipoxin receptors. ScientificWorldJournal 7:1393-1412). Orthologues of the human FPR2/ALX have been identified in the mouse (Takano, T., S. Fiore, J. F. Maddox, H. R. Brady, N. A. Petasis, and C. N. Serhan. 1997. Aspirin-triggered 15-epi-lipoxin A4 (LXA4) and LXA4 stable analogues are potent inhibitors of acute inflammation: evidence for anti-inflammatory receptors. J Exp Med 185:1693-1704) and rat (Chiang, N., T. Takano, M. Arita, S. Watanabe, and C. N. Serhan. 2003. A novel rat lipoxin A4 receptor that is conserved in structure and function. Br J Pharmacol 139:89-98). In addition to LXA4, FPR2/ALX is activated by the glucocorticoid-induced protein annexin-1 and its N-terminal peptides (Ferretti, M., N. Chiang, M. La, I. M. Fierro, S. Marullo, S. J. Getting, E. Solito, and C. N. Serhan. 2002. Endogenous lipid- and peptide-derived anti-inflammatory pathways generated with glucocorticoid and aspirin treatment activate the lipoxin A4 receptor. Nat Med 8:1296-1302), representing the first identified GPCR able to mediate anti-inflammatory and pro-resolving actions of both lipid and peptide endogenous mediators. Recently, activation of FPR2/ALX by the omega 3-derived pro-resolution mediator, Resolvin D1 has been reported (Krishnamoorthy, S., A. Recchiuti, N. Chiang, S. Yacoubian, C. H. Lee, R. Yang, N. A. Petasis, and C. N. Serhan. 2010. Resolvin D1 binds human phagocytes with evidence for proresolving receptors. *Proc Natl Acad Sci USA* 107:1660-1665) further supporting the relevance of this receptor in inflammation resolution. On the other hand, FPR2/ALX can trigger pro-inflammatory signaling when activated by some microbial and mitochondrial peptides (Romano, M., I. Recchia, and A. Recchiuti. 2007. Lipoxin receptors. *ScientificWorldJournal* 7:1393-1412) raising the question of its pathophysiological significance in vivo. This question has been addressed by gene manipulation studies. Overexpression of human FPR2/ALX in myeloid cells of transgenic mice reduced neutrophil infiltration in a model of zymosan-induced peritonitis in vivo in the absence of exogenously added agonists (Devchand, P. R., M. Arita, S. Hong, G. Bannenberg, R. L. Moussignac, K. Gronert, and C. N. Serhan. 2003. Human ALX receptor regulates neutrophil recruitment in transgenic mice: roles in inflammation and host defense. FASEB J 17:652-659). Moreover, genetic deletion of the murine orthologue of human FPR2/ALX resulted in a more pronounced inflammatory phenotype, with lack of resolution and no response to annexin 1 and LXA4 (Dutton, N., R. Hannon, V. Brancaleone, J. Dalli, H. B. Patel, M. Gray, F. D'Acquisto, J. C. Buckingham, M. Perretti, and R. J. Flower. 2010. Anti-inflammatory role of the murine formyl-peptide receptor 2: ligand-specific effects on leukocyte responses and experimental inflammation. *J Immuno*/184: 2611-2619). Along these lines, 15-epi-LXA4 biosynthesis and FPR2/ALX expression determine the magnitude and duration of the inflammatory reaction in humans (Morris, T., M. Stables, P. Colville-Nash, J. Newson, G. Bellingan, P. M. de Souza, and D. W. Gilroy. 2010. Dichotomy in duration and severity of acute inflammatory responses in humans arising from differentially expressed proresolution pathways. *Proc Natl Aced Sci USA* 107:8842-8847). Furthermore, decreased LXA4 biosynthesis and FPR2/ALX expression have been observed in asthmatic patients (Levy, B. D., C. Bonnans, E. S. Silverman, L. J. Palmer, G. Marigowda, and E. Israel. 2005. Diminished lipoxin biosynthesis in severe asthma. *Am J Respir Crit. Care Med* 172:824-830; Planaguma, A., S. Kazani, G. Marigowda, O. Haworth, T. J. Mariani, E. Israel, E. R. Bleecker, D. Curran-Everett, S. C. Erzurum, W. J. Calhoun, M. Castro, K. F. Chung, B. Gaston, N, N. Jarjour, W. W. Busse, S. E. Wenzel, and B. D. Levy. 2008. Airway lipoxin A4 generation and lipoxin A4 receptor expression are decreased in severe asthma. *Am J Respir Crit Care Med* 178:574-582). These observations support the anti-inflammatory, pro-resolution function of the LXA4-FPR2/ALX axis, whose impairment may represent an underlying pathogenetic mechanism of inflammatory chronic diseases.

WO2005047899, Nash e al., in the name of ACADIA PHARMACEUTICALS, INC published on 26 May 2005 discloses selective agonists of FPRL1 receptor of general formula:

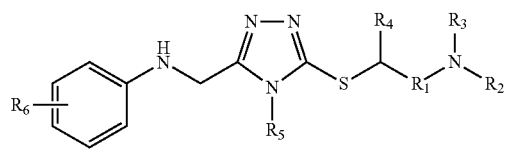

For the treatment of inflammatory conditions and their use for selecting anti-inflammatory and analgesic drugs.

US2002052529 published on 16 May 2002 and the corresponding international application WO2001068839 in the name of BAYER AKTIENGESELLSCHAFT published on 20 Sep. 2001 disclose nucleotide sequences encoding for a lipoxin A4 receptor-like polypeptide.

Examples of drug screening methods are disclosed for example in WO2002020759 and WO2003102026.

U.S. Pat. No. 6,245,512 discloses the cloning and characterization of the VEGF receptor gene promoter (Flt-1).

SUMMARY

Technical Problem

Lipoxin (LX) A4, a main endogenous stop-signal of inflammation, activates the G protein-coupled receptor FPR2/ALX, which is highly expressed in myeloid cells and triggers anti-inflammatory signaling, in vivo. Thus, the mechanisms of FPR2/ALX expression may have potential pathophysiological and therapeutic relevance.

Despite of accumulating evidence that FPR2/ALX expression level may have pathophysiological relevance, mechanisms that regulate this expression are poorly understood. Enhanced expression by glucocorticoids and selected cytokines has been documented (Sawmynaden, P., and M. Perretti. 2006. Glucocorticoid upregulation of the annexin-A1 receptor in leukocytes. Biochem Biophys Res Commun 349:1351-1355; Gronert, K., A. Gewirtz, J. L. Madara, and C. N. Serhan. 1998. Identification of a human enterocyte lipoxin A4 receptor that is regulated by interleukin (IL)-13 and interferon gamma and inhibits tumor necrosis factor alpha-induced IL-8 release. J Exp Med 187:1285-1294) but no information is currently available on the FPR2/ALX transcription machinery.

The search of the FPR2/ALX promoter has been unfruitful for almost two decades despite of the substantial effort of a number of investigators worldwide. Initial attempts by the inventors were based on the FPR2/ALX gene structure reported by Murphy (SEQ. ID. NO. 1) (Murphy, P. M., T. Ozcelik, R. T. Kenney, H. L. Tiffany, D. McDermott, and U. Francke. 1992. A structural homologue of the N-formyl peptide receptor. Characterization and chromosome mapping of a peptide chemoattractant receptor family. J Biol Chem 267: 7637-7643).

Murphy et al. discloses a mRNA sequence of FPR2/ALX deriving from alternative splicing, comprising an open reading frame (ORF) of 1056 bp and a 5'-end with an intronic sequence followed by an exon.

The sequence found by Murphy, however, does not comprise the regulatory sequences.

For this reason the FPR2/ALX promoter could not be identified on the base of the Murphy's sequence.

On the contrary, the proponents of the present invention based their investigation on a different mRNA species, deriving from alternative splicing and corresponding to the virtual genome asset labeled as c in FIG. 1A. This species comprises the ORF described by Murphy, but displays a larger intronic sequence at the 5'-end and an exon upstream of the exon identified by Murphy.

Therefore, the TSS and the gene promoter were identified on the base of said sequence, by localizing the FPR2/ALX transcription start site (TSS) and mapping a core promoter sequence of 346 bp.

More in details, SEQ. ID. NO.1 is the FPR2/ALX gene structure reported by Murphy, wherein capital letters indicate the open reading frame:

(SEQ ID NO: 1)
aggaccaggaacaacctatttgcaaagttggcgcaaacattcctgcctgacaggaccatggacaca ggttgtagagatagagatggctctggctgtgcattcagcagattctgtagatagaattaataggacttgg atgggattgtggtgagagaaagtgaaatgaaagataagttctagtttggaagttttaacaactgaatgt ttaaactcaaatagacacaaaatattggaagagtggcaggtttgggaggatgagacaatcaactgttt ggttgagccacgttaggtttgaaatgtctacgggactcccgtggggagaggttatatcagactggagc accagagagaggccaaggctgatagtttagatgaaaagagagcatgatattttaagccctgagac tggataatatcacctatagaaagactatatagagataagagaggtggggaacaagtaaaagctgc gggacactcctaaatttagagtcaaatttagagcagaaaatactagcaaagggactgaaaagc ggtggccaattgagcttcaaatgcaagtgaaagtgtgttgtgtgtacatttatcatctcatggcac aggaaaaacgtgatttaaggagaaggaagcgatccaatgggaagaagagatccaatggatcctctat cacgaagatattgagataagaaccaatatggatttgcacccactgcatttgcagccttgaggtcata agcatcctcaggaaaatgcaccaggtgctgctggcaagATGGAAACCAA

CTTCTCCACTCCTCTGAATGAATATGAAGAAGTGTCCTATGAGTCTGCTGGCTACACTGTTC

TGCGGATCCTCCCATTGGTGGTGCTTGGGGTCACCTTTGTCCTCGGGGTCCTGGGCAATG

GGCTTGTGATCTGGGTGGCTGGATTCCGGATGACACGCACAGTCACCACCATCTGTTACC

TGAACCTGGCCCTGGCTGACTTTTCTTTCACGGCCACATTACCATTCCTCATTGTCTCCATG

GCCATGGGAGAAAAATGGCCTTTTGGCTGGTTCCTGTGTAAGTTAATTCACATCGTGGTGG

ACATCAACCTCTTTGGAAGTGTCTTCTTGATTGGTTTCATTGCACTGGACCGCTGCATTTGT

GTCCTGCATCCAGTCTGGGCCCAGAACCACCGCACTGTGAGTCTGGCCATGAAGGTGATC

GTCGGACCTTGGATTCTTGCTCTAGTCCTTACCTTGCCAGTTTTCCTCTTTTTGACTACAGT

AACTATTCCAAATGGGGACACATACTGTACTTTCAACTTTGCATCCTGGGGTGGCACCCCT

GAGGAGAGGCTGAAGGTGGCCATTACCATGCTGACAGCCAGAGGGATTATCCGGTTTGTC

ATTGGCTTTAGCTTGCCGATGTCCATTGTTGCCATCTGCTATGGGCTCATTGCAGCCAAGA

TCCACAAAAAGGGCATGATTAAATCCAGCCGTCCCTTACGGGTCCTCACTGCTGTGGTGG

CTTCTTTCTTCATCTGTTGGTTTCCCTTTCAACTGGTTGCCCTTCTGGGCACCGTCTGGCTC

AAAGAGATGTTGTTCTATGGCAAGTACAAAATCATTGACATCCTGGTTAACCCAACGAGCTC

CCTGGCCTTCTTCAACAGCTGCCTCAACCCCATGCTTTACGTCTTTGTGGGCCAAGACTTC

CGAGAGAGACTGATCCACTCCCTGCCCACCAGTCTGGAGAGGGCCCTGTCTGAGGACTCA

GCCCCAACTAATGACACGGCTGCCAATTCTGCTTCACCTCCTGCAGAGACTGAGTTACAGG

CAATGTGAggatggggtcagggatattttgagttctgttcatcctaccctaatgccagttcc agcttcatctacccttgagtcatattgaggcattcaaggatgcacagctcaagtatttat tcaggaaaaatgcttttgtgtccctgatttggggctaagaaatagacagtcaggctact aaaatattagtgttattttttgttttttgacttctgcctatacctggggtaagtggagtt gggaaatacaagaagagaaagaccagtggggatttgtaagacttagatgagatagcgcataat aaggggaagactttaaagtataaagtaaaatgtttgctgtaggttttttatagctattaaa -continued

```
aaaaatcagattatggaagttttcttctattttagtttgctaagagttttctgtttcttt ttcttacatcatgagtggactttgcattttatcaaatgcattttctacatgtattaagatg gtcatattattcttcttcttttatgtaaatcattataaataatgttcattaagttctgaat gttaaactactcttgaattcctggaataaaccacacttagtcctgatgtactttaaata tttatatctcacaggagttggttagaatttctgtgtttatgtttatatactgttattt cacttttttctactatccttgctaagttttcatagaaaataaggaacaaagagaaact tgtaatggtctctgaaaaggaattgagaagtaattcctctgattctgttttctggtg ttatatctttattaaatattcagaaaaattcaccagtg
```

Whereas SEQ. ID. NO.2 is the FPR2/ALX sequence utilized for the present invention, wherein capital letters indicate the open reading frame:

(SEQ ID NO: 2)
```
tcatatttgggcttgattgcgtggctgaaactcttcccacttcagtaattgtttctttcattttca tgaaactctgaagaaggaagggctggacattcagattccttgacccttgacatttggaagcat gaactccagtctctcacagaaggctagaggtgaaggaacattcagacacattggtttctaa gaagagtccgctgacaacatacccaaggtgtcttctgaaaattataagaaatcctgagtttct gttagggattggctccagctccattgtccctcccccatcattcagtagtctccgcgaaagc ccttagagccggtgttgctccacaggaagccaagaagcacacaggaaaaggagcttagct gctggtgctgctggcaagATGGAAACCAACTTCTCCACTCCTCTGAATGAATATGAA

GAAGTGTCCTATGAGTCTGCTGGCTACACTGTTCTGCGGATCCTCCCATTGGTGGTGCTTG

GGGTCACCTTTGTCCTCGGGGTCCTGGGCAATGGGCTTGTGATCTGGGTGGCTGGATTCC

GGATGACACGCACAGTCACCACCATCTGTTACCTGAACCTGGCCCTGGCTGACTTTTCTTT

CACGGCCACATTACCATTCCTCATTGTCTCCATGGCCATGGGAGAAAAATGGCCTTTTGGC

TGGTTCCTGTGTAAGTTAATTCACATCGTGGTGGACATCAACCTCTTTGGAAGTGTCTTCTT

GATTGGTTTCATTGCACTGGACCGCTGCATTTGTGTCCTGCATCCAGTCTGGGCCCAGAAC

CACCGCACTGTGAGTCTGGCCATGAAGGTGATCGTCGGACCTTGGATTCTTGCTCTAGTC

CTTACCTTGCCAGTTTTCCTCTTTTTGACTACAGTAACTATTCCAAATGGGGACACATACTG

TACTTTCAACTTTGCATCCTGGGGTGGCACCCCTGAGGAGAGGCTGAAGGTGGCCATTAC

CATGCTGACAGCCAGAGGGATTATCCGGTTTGTCATTGGCTTTAGCTTGCCGATGTCCATT

GTTGCCATCTGCTATGGGCTCATTGCAGCCAAGATCCACAAAAAGGGCATGATTAAATCCA

GCCGTCCCTTACGGGTCCTCACTGCTGTGGTGGCTTCTTTCTTCATCTGTTGGTTTCCCTTT

CAACTGGTTGCCCTTCTGGGCACCGTCTGGCTCAAAGAGATGTTGTTCTATGGCAAGTACA

AAATCATTGACATCCTGGTTAACCCAACGAGCTCCCTGGCCTTCTTCAACAGCTGCCTCAA

CCCCATGCTTTACGTCTTTGTGGGCCAAGACTTCCGAGAGACTGATCCACTCCCTGCCC

ACCAGTCTGGAGAGGGCCCTGTCTGAGGACTCAGCCCCAACTAATGACACGGCTGCCAAT

TCTGCTTCACCTCCTGCAGAGACTGAGTTACAGGCAATGTGAggatggggtcagggatatt ttgagttctgttcatcctaccctaatgccagttccagcttcatctacccttgagtcatat tgaggcattcaaggatgcacagctcaagtatttattcaggaaaaatgctttgtgtccc tgatttggggctaagaaatagacagtcaggctactaaaatattagtgttatttttgttt tttgacttctgcctatacccctgggtaagtggagttgggaaatacaagaagagaaagac cagtggggatttgtaagacttagatgagatagcgcataataaggggaagactttaaagtat
```

-continued

```
aaagtaaaatgtttgctgtaggttttttatagctattaaaaaaaatcagattatggaagtt ttcttctattttttagtttgctaagagttttctgtttcttttttcttacatcatgagtggact ttgcattttatcaaatgcattttctacatgtattaagatggtcatattattcttcttcttttatgt aaatcattataaataatgttcattaagttctgaatgttaaactactcttgaattcctggaataaa ccacacttagtcctgatgtactttaaatatttatatctcacaggagttggttagaatttctgt gtttatgtttatatactgttatttcactttttctactatccttgctaagttttcatagaaaataagg aacaaagagaaacttgtaatggtctctgaaaaggaattgagaagtaattcctctgattctgttttct aaaattcaccagtgggtgttatatctttattaaatattcagaaaaattcaccagtg
```

15

Theoretically, the promoter should have mapped upstream of the open reading frame or of the exon of the above SEQ. ID. NO. 1, but the gene promoter was never identified in the Murphy's sequence.

On the contrary, the inventors identified the core promoter sequence because they designed an alternative strategy, based on the reconstitution of the asset of the FPR2/ALX gene through the identification of the mRNA more abundant in cells (FIG. 1A). This approach led to the discovery that post-transcriptional editing links the 5'-end of the open reading frame to the 3'-end of an exon, which is localized way upstream of the exon initially reported by Murphy. This approach enabled the inventors to design the strategy to map the FPR2/ALX promoter. The first step was to localize the TSS by 5' rapid amplification of DNA ends (RACE) analysis.

Due to the relatively low abundance of FPR2/ALX mRNA species, the manufacturer's instructions provided with the 5' RACE kit (Invitrogen) were modified in using a gene specific reverse primer, instead of the Oligo dT reverse primer indicated by the manufacturer, in order to amplify the mature mRNA species to which an RNA oligo had been ligated at the 5' end. This modification permitted the enrichment of the FPR2/ALX mRNA sequences, thus minimizing the amplification of non-specific mRNAs and allowing the correct TSS mapping.

Once localized the TSS, a 1500 bp sequence upstream the TSS was cloned into a reporter plasmid and tested for promoter activity.

Said sequence showed strong luciferase activity in reporter gene assay. The chromatin immuno-precipitation revealed the presence of an Sp1 binding site within the core promoter. Site-directed mutagenesis of this site and Sp1 overexpression showed that this transcription factor is key for maximal promoter activity, which is instead inhibited by DNA methylation.

A single nucleotide mutation, -220 bp from the TSS, was detected in a subject with history of cardiovascular disease and in his two daughters. This mutation reduced by -35-90% the promoter activity in vitro. Consistent with this, individuals carrying this mutation displayed respectively -10 and 3 fold reduction in FPR2/ALX mRNA and protein levels in PMN compared to normal subjects and their relatives without the mutation.

The inventors of the present invention also provided evidence of mutations that affect FPR2/ALX expression at the transcriptional level and are correlated with inflammatory disorders.

Moreover, the inventors of the present invention found that the full promoter sequence (P-1500) comprises repressive sequences whose activation has a repressive effect on the activity of the promoter and, therefore, the expression of FPR2/ALX can be inhibited by repressive complexes likely operating upstream of the core promoter.

In the field of pharmaceutical and more in particular of personalized medicine, there is a strong felt need of screening assay for new anti-inflammatory molecules and od diagnostic tools for detecting the presence and/or the risk of developing inflammatory diseases or events.

The identification of the FPR2/ALX promoter and of the mutation related to inflammatory diseases allowed to obtain a cellular expression system useful for the screening of molecules, which influence the promoter and affect FPR2/ALX expression.

Furthermore, said system is useful for assessing if a subject is at risk of inflammatory diseases and cardiovascular diseases in particular, and their responsiveness to drugs.

OBJECTS OF THE INVENTION

Object of the present invention are the promoter sequences of the FPR2/ALX gene in their wild type form, their mutated forms and their forms comprising a SNP and the expression vectors and cell lines comprising said sequences.

A further object of the present invention is the use of the above sequences as a tool in a screening system for anti-inflammatory drug discovery, wherein the screening system comprises a cell line transfected with a vector comprising a core promoter sequence wild type or mutated and a reporter gene.

Further object of the present invention is a method for identifying active ingredients for preventing or treating inflammatory diseases comprising a step of adding said active ingredient to the screening system and a step of detecting the activity of said active ingredient on the expression of the reporter gene.

Still another object of the present invention is a method for determining whether a subject has, or is at risk of developing inflammatory diseases, comprising determining the presence or absence of a variant allele A/G of nucleotide polymorphism (SNP) of the core promoter sequence wherein homozygosis or heterozygosis for the G allele indicates that the individual is at risk for cardiovascular disease.

A further object of the present invention is a method for predicting the responsiveness of a subject at risk of having or developing an inflammatory disease and/or an inflammatory event, to a drug stimulating the activity of the FPR2/ALX gene promoter comprising a step of adding said active ingredient to two screening system, wherein one expressing the wild type and the other expressing the FPR2/ALX gene promoter sequence with a SNP, in parallel; a step of detecting the responsiveness of the wild type and promoter sequence with a SNP to said active ingredient and a step of comparing the expression of the reporter gene in the cell line expressing the wild type with the expression of the reporter gene in the cell line expressing promoter sequence with a SNP.

A further object of the present invention are kits comprising the screening system suitable reagents for their use together, sequentially and separately.

Further characteristics of the present invention would be clear from the following detailed description with reference to the experimental examples and the attached sheets of drawings.

BRIEF DESCRIPTION OF THE FIGURES

FIG. 1B-C-D shows: panels B and C the analysis of FPR2/ALX transcripts in respectively THP1 and MDA-MB231 cells. Lane 1, 524 bp cassette of exon 1 in sequence c of FIG. 1A; Lane 2, full-length FPR2/ALX transcript (1056 bp); Lane 3, GAPDH control. Images were acquired using the Chemi Doc System. Panel D shows the 5' RACE analysis. Product from PCR amplification of purified total RNA with For GeneRace Nested and Rev Gene Nested primers (left panel). The 5'-terminus sequence of this product is reported in the right panel. Nucleotides from exon 1 are in uppercase and the TSS (+1) is indicated by the arrow. Nucleotides from the open reading frame are in lowercase and the start codon is in boldface type.

DETAILED DESCRIPTION OF THE INVENTION

Definitions

Figure 1A:
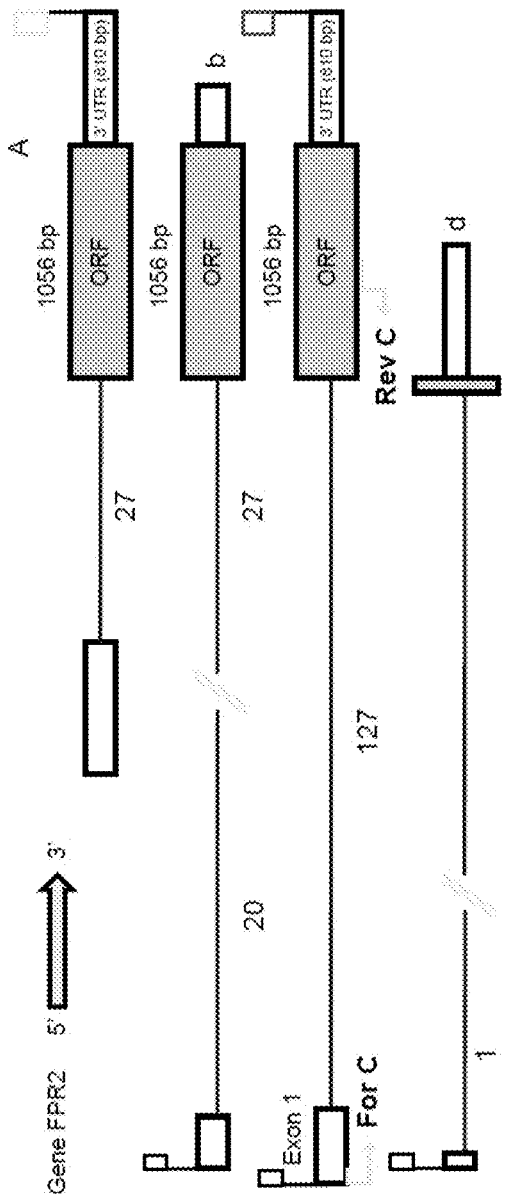
FIG. 1A shows the localization of the TSS in the FPR2/ALX gene. Sequence named A is a schematic map of the FPR2/ALX gene. Alternative mRNAs are shown aligned from 5' to 3' on a virtual genome where introns have been shrunk to a minimal length. Exon size is proportional to length. The map of gene is modified from NCBI AceView (http://www. ncbi.nlm.nih.gov/IEB/Research/Acembly/index.html). Arrows represent specific primers used to amplify the first exon in the sequence named sequence c (expected length 524 bp).

Within the meaning of the present invention, core promoter sequence means the minimal sequence within the promoter required to initiate gene transcription.

Within the meaning of the present invention, screening system means an expression vector comprising the core promoter sequence and a reporter gene whose expression is controlled by said core promoter sequence, wherein the molecules to be screened act on the promoter.

Within the meaning of the present invention, expression vector means a vector wherein a coding sequence is inserted to be transcribed and translated into a protein.

Within the meaning of the present invention, reporter gene means a sequence encoding for a product, which is easily detected.

Within the meaning of the present invention, epigenetic regulation means regulation of gene expression by mechanisms other than changes in the underlying DNA sequence.

Within the meaning of the present invention, inflammatory disorder means conditions involving abnormal and/or chronic inflammation.

Within the meaning of the present invention allergy, myopathies, immune system disorders, cancer, cardiovascular diseases, atherosclerosis, ischemic heart disease, spondylitis, gout, psoriasis, osteoarthritis, systemic lupus erythematosus (SLE) and juvenile arthritis, asthma, bronchitis, menstrual cramps, tendinitis, bursitis, and skin related conditions such as psoriasis, eczema, burns and dermatitis; gastrointestinal conditions such as inflammatory bowel disease, Crohn's disease, gastritis, irritable bowel syndrome and ulcerative colitis; inflammation in such diseases as vascular diseases, migraine headaches, periarteritis nodosa, thyroiditis, aplastic anemia, Hodgkin's disease, sclerodoma, rheumatic fever, vasculitis, Alzheimer's disease, acute respiratory distress syndrome (ARDS), myasthenia gravis, multiple sclerosis, sarcoidosis, nephrotic syndrome, Behcet's syndrome, polymyositis, gingivitis, hypersensitivity, swelling occurring after injury, and myocardial ischemia; ophthalmic diseases, such as retinitis, retinopathies, conjunctivitis, uveitis, ocular photophobia, and of acute injury to the eye tissue; pulmonary inflammation, such as that associated with viral infections and cystic fibrosis, are examples of inflammatory disease.

Within the meaning of the present invention, cardiovascular disease means any disease that affects the cardiovascular system.

Within the meaning of the present invention thrombosis, stroke, atherosclerosis, coronary artery disease, ischemic cerebrovascular disease, peripheral vascular disease, and other at hero-thrombotic events are examples of cardiovascular diseases.

Within the meaning of the present invention endogenous gene means a gene being naturally present in the cell.

Within the meaning of the present invention exogenous gene means a gene introduced in the cell by means of transfection.

Within the meaning of the present invention transition means a point mutation exchanging a purine for a purine (A ↔ G) or a pyrimidine for a pyrimidine, (C ↔ T).

Within the meaning of the present invention transversion means a point mutation exchanging a purine for a pyrimidine or a pyrimidine for a purine (C/T ↔ A/G).

Within the meaning of the present invention Sp1 binding site means the binding site on the DNA for the human transcription factor Sp1 (Specificity Protein 1)

In the present invention the core promoter sequence of the FPR2/ALX gene is the wild type sequence or a methylated for of the wild type sequence or a wild type sequence mutated in the Sp1 binding site or containing a SNP.

In a preferred embodiment the wild type sequence of the FPR2/ALX gene is selected from the group consisting of Core promoter sequence of FPR2/ALX gene, wild type named P-346 (Sp1 binding site in bold) (SEQ: ID: NO. 3)

GGCTGAAACTCTTCCCACTTCAGTAATTGTTTCTTTCATTTTCATGAAACTCTGAAGAAGGA

AGGGCTGGACATTCAGATTCCTTGACCCTTGACATTTGGAAGCATGAACTCCAGTCTCTCA

CAGAAGGCTAGAGGTGAAGGAACATTCAGACACATTGGTTTCTAAGAAGAGTCCGCTGACA

ACATACCCAAGGTGTCTTCTGAAAATTATAAGAAATCCTGAGTTTCTGTTAGGGGATTGGCT

CCAGCTCCATTGTCCCTCCCCCATCATTCAGTAGTCTCCGCGAAAGCCCTTAGAGCCGGT

GTTGCTCCACAGGAAGCCAAGAAGCACACAGGAAAAGGAG or

FPR2/ALX gene, wild type named P-1500 (SEQ. ID. NO. 4)

TAATGCTTATTGCTGTCTGCCTTATCATCTATGCTCTGGTAAACAAAAGTAACCTGCTTTTTT

GTGACCCCTTTCGTGGGTATTTTTACTCCCCTCTGACAAGAATGCATTATTTTTTCTCCTTTA

TCTGAGTCTTTAAGACTCAGCCTACATGTTCCCTCCTCCGGATATTGACTCTAGATCCGTGA

ATCTGAGTTAGTGGTTCCTTTTAGAGGACCTCACAAGGAGCCAGGCATCTGTCTATCACTA

CGTGCCCCCACCCTATTGTAACTAAGCACTGCATTCTCACCTCTCTATTCAGGTGGTCCGC

AGAGCCCATGTCTGATTGATCTCTATGTCTCCAGCAGCCAGCAAGGAAGCACCTCTTTAGA

GACCTGCACCTATACAATACCTACCACCTTTTATTTCTCGATATGTGAACTCCATTGAGAAC

AAACGAGTAAATGTAGGTAATGTGCCTTCTTCTTTTCTTTTCTTTTCTTTTTTTTTTAGATGG

AGTCTCGCTCTGTTGCCCAGGCTGGAGTTTAGTGGCACAATCTCGGCTCACTGTAACCTCC

GCCTCCCAGGTTCAAGCGATTCTGCCGCCTCAGCCTACCAAGTAGTTGGGATTACAGGTG

-continued

```
CCCACCACCACGCCCAGCTAATTTTTTTTGTATTTTTAGTAGAGGTGGGGTTTCATGATGTT

GGCTAGGATGGTTTTCAACTCCTGACCTCAAGTGATCCACCCACCTCGGCCTCCCAAAGTG

CTAGGATTACAGGTGTGAGCCACAGCGCCCAGCCAGTAATGTGCCTTCTTAAGTTCTGTGA

GCCATTCTAACAAATTATCAGAACAGAGGAAGGGGTTATAAACATCCCCCCACCCCCGATT

TATAGCCAGTCAGTCAGAAGTACAGGTGGCCACCTGGGACTTGGATTGGTGTCTGAAGTG

AGGACAGTTTTGGGAGAGTGAGCCCTTTAACTTGTGGGATCTGACACTAACTCCAGGTAGA

CAGCGTCGGAGCTGAATTGAATTGTGAGATACCCAGTGGTGTCCCCAGAGAACTGGAGAA

TTGCTTGATATGGAAAAGACCCACACATTTGATGCCAGAAGTACTGCATAAGTCGAGAATT

GAGTTTGACTTAATCATCATATTTGGGCTTGATTGCGTGGCTGAAACTCTTCCCACTTCAGT

AATTGTTTCTTTCATTTTCATGAAACTCTGAAGAAGGAAGGGCTGGACATTCAGATTCCTTG

ACCCTTGACATTTGGAAGCATGAACTCCAGTCTCTCACAGAAGGCTAGAGGTGAAGGAACA

TTCAGACACATTGGTTTCTAAGAAGAGTCCGCTGACAACATACCCAAGGTGTCTTCTGAAA

ATTATAAGAAATCCTGAGTTTCTGTTAGGGGATTGGCTCCAGCTCCATTGTCCCTCCCCCAT

CATTCAGTAGTCTCCGCGAAAGCCCTTAGAGCCGGTGTTGCTCCACAGGAAGCCAAGAAG

CACACAGGAAAAGGAG
```

In a more preferred embodiment the Core promoter sequence of FPR2/ALX gene wild type is P-346 (SEQ: ID: NO. 3).

In a preferred embodiment the core promoter sequence of the FPR2/ALX gene mutated in the Sp1 binding site is P-346mut (mutated bases underlined) (SEQ: ID: NO. 5)

The above sequences are used in a screening system for anti-inflammatory and/or cardiovascular drug discovery and the screening method thereof.

The screening system comprises a cell line, transfected with an expression vector comprising said core promoter sequence and a reporter gene.

```
GCGTGGCTGAAACTCTTCCCACTTCAGTAATTGTTTCTTTCATTTTCATGAAACTCTGAAGA

AGGAAGGGCTTTACATTCAGATTCCTTGACCCTTGACATTTGGAAGCATGAACTCCAGTCT

CTCACAGAAGGCTAG AGGTGAAGGAACATTCAGACACATTGGTTTCTAAGAAGAGTCCGCT

GACAACATACCCAAGGTGTCTTCTGAAAATTATAAGAAATCCTGAGTTTCTGTTAGGGGATT

GGCTCCAGCTCCATTGTCCCTCCCCCATCATTCAGTAGTCTCCGCGAAAGCCCTTAGAGCC

GGTGTTGCTCCACAGGAAGCCAAGAAGCACACAGGAAAAGGAGCTTAGCTGCTGGTAAG
```

In a preferred embodiment the methylated core promoter sequence of FPR2/ALX gene is methylated in CCGG motif and/or CpG motif.

In a preferred embodiment the core promoter sequence of the FPR2/ALX gene contains an SNP wherein the SNP is a A/G transition point mutation.

In a more preferred embodiment the core promoter sequence of FPR2/ALX gene with SNP is (SEQ: ID: NO 6) (mutated base in bolt)

The cell line can be any cell line expressing the endogenous FPR2/ALX gene, in order to furnish appropriate transcriptional and translational apparatus for exogenous genes herein transfected.

The cell line is preferably human.

More preferably the cell line is selected from the group consisting of MDA-MB231, MCF-7 or 16HBE.

In a preferred embodiment the cell line is MDA-MB231.

```
GGCTGAAACTCTTCCCACTTCAGTAATTGTTTCTTTCATTTTCATGAAACTCTGAAGAAGGA

AGGGCTGGACATTCAGATTCCTTGACCCTTGACGTTTGGAAGCATGAACTCCAGTCTCTC

ACAGAAGGCTAGAGGTGAAGGAACATTCAGACACATTGGTTTCTAAGAAGAGTCCGCTGAC

AACATACCCAAGGTGTCTTCTGAAAATTATAAGAAATCCTGAGTTTCTGTTAGGGGATTGGC

TCCAGCTCCATTGTCCCTCCCCCATCATTCAGTAGTCTCCGCGAAAGCCCTTAGAGCCGGT

GTTGCTCCACAGGAAGCCAAGAAGCACACAGGAAAAGGAG
```

The vector comprises one of the nucleotide sequences as disclosed above and a reporter gene.

Preferably the expression vector is selected from the group consisting of pGL3 or PgL4.

In a preferred embodiment the expression vector is pGL3.

The expression vector can be prepared by conventional methods.

Preferably the reporter gene is selected from the group consisting of luciferase gene or green fluorescent protein gene.

In a preferred embodiment the reporter gene is luciferase gene.

A most preferred embodiment is a pGL3 expression vector comprising the core promoter sequence and luciferase gene.

Said pGL3 expression vector is prepared by linking a core promoter sequence into pGL3 previously digested with Kpn I and Xho I restriction endonucleases.

A more preferred embodiment is MDA-MB231 cell line transfected with pGL3 expression vector comprising a core promoter sequence and luciferase gene.

Drug discovery is carried out by means of a method for identifying anti-inflammatory active ingredients, said method comprises a step of adding said active ingredient to the screening system as disclosed above and a step of detecting the activity of said active ingredient on the expression of the reporter gene.

In a preferred embodiment, in the screening system used in the method for drug discovery a wild type core promoter sequence of the FPR2/ALX gene is used.

In most preferred embodiments the sequence is SEQ. ID. NO. 3 or SEQ. ID. NO. 4.

In the method for determining whether a subject has, or is at risk of developing inflammatory diseases, the presence or absence of a variant allele A/G of nucleotide polymorphism (SNP) of the core promoter sequence is determined, homozygosis or heterozygosis for the G allele indicates that the individual is at risk for cardiovascular disease. In a preferred embodiment of said method preferably is used a SNP which is a A/G transition point mutation and more preferably is SEQ.ID.NO.5.

In a further preferred embodiment the presence or absence of a variant allele A/G of nucleotide polymorphism (SNP) of the core promoter sequence is determined by nucleic acid sequencing and/or PCR analysis.

The method for predicting the responsiveness of a subject at risk of having or developing an inflammatory disease and/or an inflammatory event, to a drug stimulating the activity of the FPR2/ALX gene promoter comprises a step of adding said active ingredient to two screening system, wherein one expressing the wild type and the other expressing the FPR2/ALX gene promoter sequence with a SNP, in parallel; a step of detecting the responsiveness of the wild type and promoter sequence with a SNP to said active ingredient and a step of comparing the expression of the reporter gene in the cell line expressing the wild type with the expression of the reporter gene in the cell line expressing promoter sequence with a SNP.

In a preferred embodiment of the above method the wild type promoter sequence of the FPR2/ALX gene is SEQ. ID. NO. 3 or SEQ. ID. NO. 4 and the FPR2/ALX gene sequence with a SNP is SEQ. ID. NO. 6.

In the disclosed method the inflammatory disorder can be selected in the group consisting of:
allergy, myopathies, immune system disorders, cancer, cardiovascular diseases, atherosclerosis, ischemic heart disease, spondylitis, gout, psoriasis, osteoarthritis, systemic lupus erythematosus (SLE) and juvenile arthritis, asthma, bronchitis, menstrual cramps, tendinitis, bursitis, and skin related conditions such as psoriasis, eczema, burns and dermatitis; gastrointestinal conditions such as inflammatory bowel disease, Crohn's disease, gastritis, irritable bowel syndrome and ulcerative colitis; inflammation in such diseases as vascular diseases, migraine headaches, periarteritis nodosa, thyroiditis, aplastic anemia, Hodgkin's disease, scleroderma, rheumatic fever, vasculitis, Alzheimer's disease, acute respiratory distress syndrome (ARDS), myasthenia gravis, multiple sclerosis, sarcoidosis, nephrotic syndrome, Behcet's syndrome, polymyositis, gingivitis, hypersensitivity, swelling occurring after injury, and myocardial ischemia; ophthalmic diseases, such as retinitis, retinopathies, conjunctivitis, uveitis, ocular photophobia, and of acute injury to the eye tissue; pulmonary inflammation, such as that associated with viral infections and cystic fibrosis.

The cardiovascular diseases can be selected in the group consisting of: thrombosis, stroke, atherosclerosis, coronary artery disease, ischemic cerebrovascular disease, peripheral vascular disease, and other atherothrombotic events.

The invention also comprises kit of parts comprising the screening methods as disclosed and suitable reagent to carry out one of the above methods.

EXAMPLES

Example 1

Analysis of FPR2/ALX Transcripts in Human Cell Lines

Human acute monocytic leukemia cells, THP1, were cultured at starting density of $2\times10^5$/mL in Roswell Park Memorial Institute medium (RPMI 1640, PAA, Pasching, Austria) supplemented with 10% vol/vol fetal bovine serum (FBS, Invitrogen, San Giuliano Milanese, Italy), 100 U/mL penicillin and streptomycin (P/S). Cells were cultured at 37° C., 100% humidity and 5% $CO_2$. Human breast cancer MDA-MB231 cells were grown in a humidified atmosphere containing 5% $CO_2$ at 37° C. in Dulbecco's Modified Eagle Medium (DMEM, PAA) containing high glucose (4.5 g/L at 25 mM) and supplemented with 100 U/mL P/S, and 10% vol/vol FBS.

Total RNA was isolated from 80% confluent MDA-MB 231 using Rneasy Plus Mini Kit (Qiagen) according to the manufacturer's instructions. RT-PCR was performed using 100 ng of total RNA. The reaction was performed in a final volume of 20 µl using M-MLV Reverse Transcriptase (Sigma-Aldrich). Primers For C (5' GGG CTT GAT TGC GTG GC 3' (SEQ ID NO: 29)) and Rev C (5' TCA GAC AGG GCC CTC TC 3' (SEQ ID NO: 30)) were designed to amplify a sequence of 524 bp located respectively at the 5' and 3' UTRs of the FPR2/ALX gene. PCR reaction mixtures contained 100 ng of forward and reverse primers, 10 ng cDNA, 0.2 mM dNTPs, Taq DNA polymerase buffer, and 5 units of Taq DNA polymerase (Sigma-Aldrich). Mixtures were incubated for 10 min at 95° C., followed by 35 cycles of amplification (60 seconds at 95° C.; 60 s at 52° C.; 60 seconds at 72° C.). Products were separated by gel electrophoresis on 1.5% agarose gel, visualized by ethidium bromide staining and analysed using the Chemi Doc System (Bio-Rad).

The FPR2/ALX mRNA sequences expressed in the human cell lines MDA-MB231 and THP1 were determined by RT-PCR. As expected, we detected the full-length 1056 bp transcript of the open reading frame, initially reported by Murphy (FIG. 1A, top and SEQ. ID. NO. 1). However, we also detected in both cell types a 524 bp product encopassing the first exon and part of the open reading frame of the sequence c in FIG. 1A. These results indicate this last sequence is the only to give complete mRNA sequences in MDA-MB231 and THP1 cells. Therefore, we focused on this sequence to map the FPR2/ALX transcription start site (TSS).

Example 2

Identification of the TSS

Table 1 reports all the sequences of primers used in examples 1-6.

1). An aliquot of the PCR products was used as template for a nested reaction with the For Gene RACE nested and Rev TSS Nested primers (Table 1). The agarose gel electrophoresis of the PCR products obtained with the For Gene Race and Rev TSS Race outer primers revealed a weak band of the expected size. This band was further amplified by nested PCR using the

TABLE 1

| | | | |
|---|---|---|---|
| SEQ. ID. NO. 7 | For Gene Race | 5' | CGA CTG GAG CAC GAG GAC ACT GA 3' |
| SEQ. ID. NO. 8 | For Gene Race Nested | 5' | GGA CAC TGA CAT GGA CTG AAG GAG TA 3' |
| SEQ. ID. NO. 9 | Rev TSS | 5' | GGT TCAGGTAACAGATGGTGGTGAC 3' |
| SEQ. ID. NO. 10 | Rev TSS Nested | 5' | AGA TCA CAA GCC CAT TGC CCA GG 3' |
| SEQ. ID. NO. 11 | For 1500 bp | 5' | TTAATGCTTATTGCTGTCTGCC 3' |
| SEQ. ID. NO. 12 | Rev 1500 bp | 5' | CTCCTTTTCCTGTGTGCTTC 3' |
| SEQ. ID. NO. 13 | For 1500 bp Kpn I | 5' | GGGGTACCTTAATGCTTATTGCTGTCTGCC 3' |
| SEQ. ID. NO. 14 | Rev 1500 bp Xho I | 5' | CCGCTCGACCTCCTTTTCCTGTGTGCTTC 3' |
| SEQ. ID. NO. 15 | P 1000 For | 5' | TTAATGCTTATTGCTGTCTGCC 3' |
| SEQ. ID. NO. 16 | P1000 Rev | 5' | AGAATGGCTCACAGAACTTAAG 3' |
| SEQ. ID. NO. 17 | P 300 For | 5' | AACAAATTATCAGAACAGAGG 3' |
| SEQ. ID. NO. 18 | P300 Rev | 5' | ACTCAATTCTCGACTTATGC 3' |
| SEQ. ID. NO. 19 | P346 | 5' | GGCTGAAACTCTTCCCAC 3' |
| SEQ. ID. NO. 20 | P 346 Rev | 5' | CCGACTTTGAGAAGGGTG 3' |
| SEQ. ID. NO. 21 | P269 | 5' | AGATTCCTTGACCCTTGAC 3' |
| SEQ. ID. NO. 22 | P 184 | 5' | TTCTAAGAAGAGTCCGCTG 3' |
| SEQ. ID. NO. 23 | P 123 | 5' | GAGTTTCTGTTAGGGATTG 3' |
| SEQ. ID. NO. 24 | P 71 | 5' | AGTAGTCTCCGCGAAAGCC 3' |
| SEQ. ID. NO. 25 | For Sp1 | 5' | CTCTGAAGAAGGAAGTTCTGGACATTCAGATT 3' |
| SEQ. ID. NO. 26 | Rev Sp1 | 5' | AATCTGAATGTCCAGAACTTCCTTCTTCAGAG 3' |
| SEQ. ID. NO. 27 | For Mut pt | 5' | GATTCCTTGACCCTTGACGTTTGGAAGCATGAACTCC 3' |
| SEQ. ID. NO. 28 | Rev Mut pt | 5' | GGAGTTCATGCTTCCAAACGYCAAGGGTCAAGGAATC 3' |
| SEQ. ID. NO. 29 | For C | 5' | GGG CTT GAT TGC GTG GC 3' |
| SEQ. ID. NO. 30 | Rev C | 5' | TCA GAC AGG GCC CTC TC 3' |

To localize the TSS of FPR2/ALX, a RNA ligase-mediated rapid amplification of 5' end (RLM-RACE) strategy was used to obtain the full-length cDNA sequence at the 5' end, using the GeneRacer™ (Invitrogen) kit. Briefly, 5 µg of total RNA from THP1 cells was used to prepare 5'-racing cDNA. The first-strand cDNA was amplified using universal forward For Gene Race and reverse gene-specific primer Rev TSS (Table 1). For Gene Race Nested and Rev TSS Nested primers. The 5'-RACE-nested PCR gave a single DNA fragment (FIG. 1D) that was cloned and sequenced.

The TSS was identified by sequence analysis and mapped 65 bp upstream the ATG translation codon inside exon 1 (SEQ. ID. NO.31)

GTTGCTCCACAGGAAGCCAAGAAGCACACAGGAAAAGGAGCTTAGCTGCTGGTGCTGCTGGCAAG atggaaaccaacttctccactcctctgaatgaatatgaagaagtgtcctatgagtctgctggctacactgttc tgcggatcctcccattggtggtgcttgggtcaccttttgtcctcgggtcctgggcaatgggcttgtgatct.

Example 3

FPR2/ALX Promoter Activity in Human Cell Lines

Figure 2:
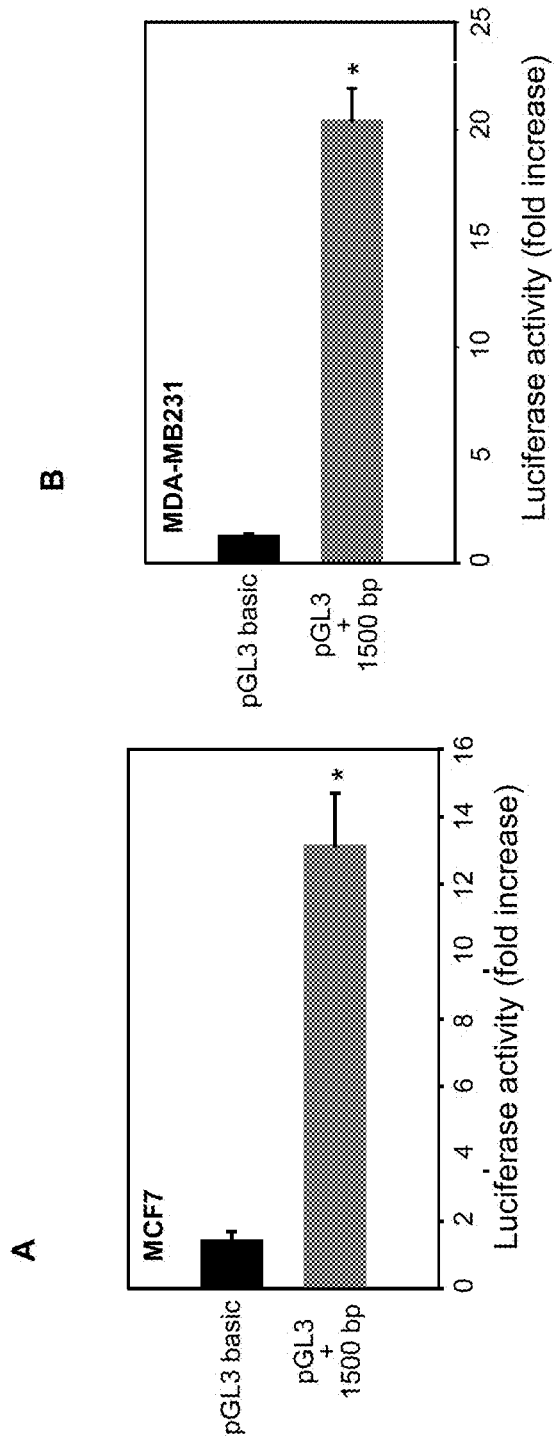
FIG. 2 shows the FPR2/ALX promoter activity in human cell lines. MCF7 (panel A) and MDA-MB231 (panel B). cells were transiently transfected with the P-1500 promoter construct (nt −1449 to +39 from the TSS) inserted into the pGL3-Basic luciferase reporter vector. Luciferase activity was measured 48 h post transfection and normalized by protein concentration. Luciferase activity is expressed as fold over that measured with lysates from cells transfected with the pGL3 basic promoterless vector. Results represent mean±S.D. from n=3 in duplicate (*, P=0.002 for MCF7 cells and 0.00024 for MDA-MB231 cells vs control vector).
Figure 3:
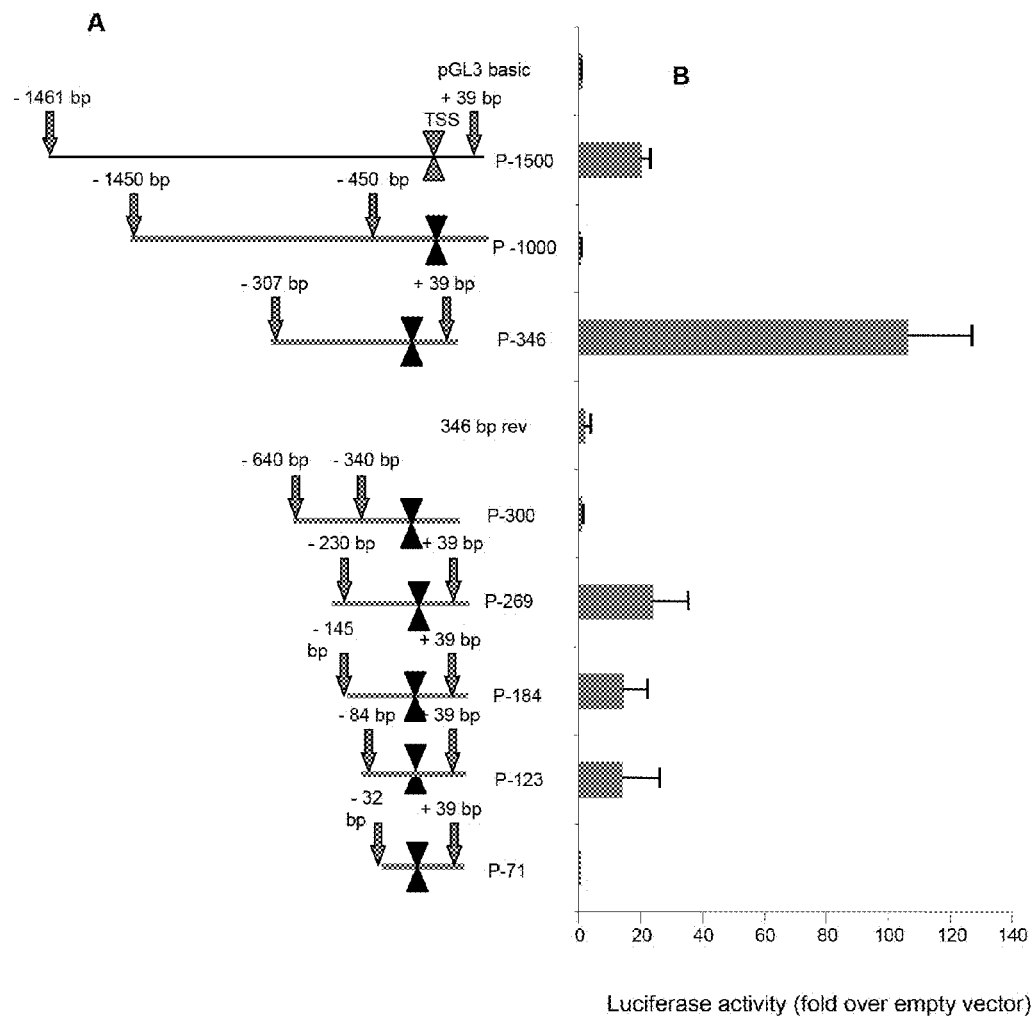
FIG. 3. Panel A shows the schematic map of a number of deletion constructs. Panel B reports the Luciferase activity of the constructs. MDA-MB231 cells were transiently transfected with nine promoter constructs, ranging from nt −1449 (P-1500) to −32 (P-71) and extending to nt +39 from the TSS. Sequences were inserted into the pGL3-Basic luciferase reporter vector. Luciferase activity was measured 48 h post-transfection and normalized by protein concentration. Luciferase activity is expressed as described in the legend to FIG. 2. Results are mean±S.D. of n=3 with duplicates.

Having localized the TSS, a 1500 bp fragment of human genomic DNA (−1449/+51 from the TSS) was amplified by PCR, cloned into the promoterless pGL3 vector containing the luciferase reporter gene. For this purpose, Genomic DNA was extracted from the THP1 cells using the Wizard Genomic DNA Purification Kit (Promega, Milan, Italy). Two primers, (For 1500 bp e Rev 1500 bp, Table 1) were designed on the basis of genomic DNA sequence of 5'-flanking region of the FPR2/ALX gene to amplify a section of DNA starting −1449 bp upstream of the identified transcription start site (+1). In addition to the template (100 ng of genomic DNA) and primers For 1500 bp and Rev 1500 bp (100 ng), the reaction mixture contained 0.2 mM dNTPs, Pfu DNA polymerase buffer and 0.05 units of Jumpstart Taq DNA polymerase (Sigma-Aldrich), PCR consisted of 35 cycles of amplification (30 seconds at 94° C., 30 s at 52° C., and 120 seconds at 72° C.). PCR products were recovered from low melting agarose gel and used as template in PCR reactions using primers For 1500 and Rev 1500, added of Kpn I and Xho I restriction sites, respectively (Table 1). PCR products were resolved by 1.5% agarose gel elecrophoresis, purified and ligated into the pGL3-basic reporter vector, which was previously digested with Kpn I and Xho I restriction endonuclease. The resulting plasmid was designated P-1500 bp and was sequenced to verify insertion and correct orientation of the cloned sequence. The promoter activity of the construct was analyzed by transfection into MCF7 and MDA-MB231 cells. FIG. 2 shows the relative luciferase activity of the reporter construct. A slightly higher activity was detected in MDA-MB231 cells (18 fold over empty vector) compared to MCF7 cells (14 fold over empty vector). Therefore, said cell line was selected for further studies. The 1500 bp sequence was scanned using the MATInspector software for the presence of putative transcription factor binding sites. Canonical TATA (−92 bp) and CAAT (−144 bp) boxes and a putative binding site for Sp1 (−234 bp) were revealed and further investigated for their functional relevance. To this end, different length sequences of the 5' flanking region were amplified by PCR and cloned into the pGL3 basic vector. The 1500 bp DNA fragment was used as template to make PCR products of sequences between −307/+39 bp (P-346), −230/+39 (P-269), −145/+39 (P-184), −1450/−450 (P-1000), −640/−340 (P-300), −84/+39 (P-123), −32/+39 (P-71) (FIG. 3A). These DNA-fragments were subcloned into pGL3 and the resulting constructs were sequenced to ensure fidelity of amplification. The above constructs were transfected into MDA-MB231 cells and tested for promoter activity. As shown in FIG. 3, P-346, encompassing Sp1, COAT and TATA binding sites, showed the highest promoter activity, ~100 fold over empty vector. This activity was completely lost when the sequence was cloned in reverse, indicating directionality of this promoter. Constructs P-1000 and P-300, localized upstream P-346, did not induce significant activity, while plasmids P-269, encompassing COAT and TATA boxes, and P-184, encompassing only TATA binding sites, showed ~20 and ~15 fold luciferase activity over empty vector, respectively. Construct P-123, which did not contain Sp1, COAT and TATA binding sites, had ~15 fold promoter activity over the pGL3 basic vector. Finally, P-71 did not show significant promoter activity. The results identify P-346 as core promoter and indicate that Sp1 may play a key role in the FPR2/ALX transcription machinery.

Example 4

Analysis of Sp1 Binding and Function

A reporter plasmid expressing P-346 with mutated Sp1 binding site was generated using mutagenic primers (For Sp1 and Rev Sp1, Table 1). Both primers annealed to the same target sequence on opposite strands of P-346. Site-directed mutagenesis was performed using the Quick Change Site-Directed Mutagenesis Kit (Stratagene) and the resulting plasmid was designated P-346 bp Sp1-mut. A reporter plasmid expressing the (A/G) SNP at −220 from the TSS in the FPR2/ALX promoter was generated using a 5'-primer annealing to −229/−213 bp from the TSS. Primers For Mut pt and Rev Mut pt (Table 1) annealed to the same target sequence on opposite strands of P-346 and the site-directed mutagenesis was performed as described above. The resulting plasmid was designated P-346 bp mut pt.

ChIP-IT Kit (Active Motif) was used to study protein/DNA interactions. Briefly, MDA-MB231 cells were crosslinked for 10 minutes at room temperature with fixation solution. Cells were scraped off and homogenized with a dounce homogenizer. Cell lysates were centrifuged (5000 rpm, 10 minutes, 4° C.) to isolate the nuclear fraction, which was suspended in shearing buffer, supplemented with protease inhibitors. After sonication on ice (10 pulses of 20 seconds) and centrifugation, supernatants were diluted in ChIP buffer and pre-cleared with Protein G beads (2 hours, 4° C.). An aliquot (10 µl) of pre-cleared chromatin was stored at −20° C. as "Input DNA". The supernatant was divided into three aliquots. One aliquot did not receive antibodies (negative control), the other two received either RNA poi II antibody or Sp1-specific antibody (Santa Cruz, Heidelberg, Germany). After incubation (16 hours, 4° C.) on a rotating wheel, protein G beads were added to each of the antibody/chromatin incubations, which were kept under rotation for 1.5 hours at 4° C. Immunoprecipitated DNA was eluted from the washed Protein G beads and crosslinking was reversed by heating at 65° C. overnight. The eluates were digested with proteinase K at 42° C. for 2 hours and the DNA was purified using mini-columns provided with the ChIP-IT Kit. The FPR2/ALX promoter region was amplified by PCR using 5'-GCTGAAACTCTTCCCACTTC-3' (forward) (SEQ.ID.NO. 37) and 5'-GAGACTGGAGTTCAT-GCTTC-3' (reverse) (SEQ.ID.NO. 32) primers which cover the FPR2/ALX promoter from −345 bp to −225 bp from the TSS. For additional control, 197 bp of glyceraldehyde-3-phosphate dehydrogenase (GAPDH) was PCR amplified using the GAPDHf and GAPDHr primers provided with kit. PCR products were visualized after separation on 1% agarose gel containing 0.5% ethidium bromide.

Figure 4A:
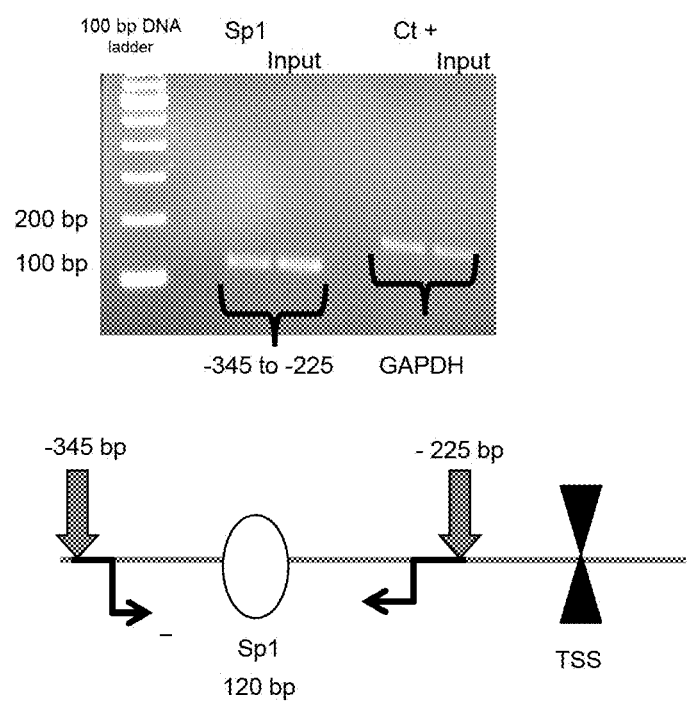
FIG. 4A shows Chromatin immunoprecipitation. Proteins from MDA-MB231 cells were cross-linked to the DNA. Protein-DNA complexes were immunoprecipitated using antibodies directed against RNA-Polymerase (control) or Sp1. Input controls were processed similarly, except for incubation with antibodies. Immunoprecipitated DNA was PCR amplified using specific primers for the FPR2/ALX promoter region bearing the putative Sp1 cis-acting element (−345 to −225 from the TSS) (lower panel) or for GAPDH. Results from one experiment representative of 3 are shown in the upper panel.
Figure 4B:
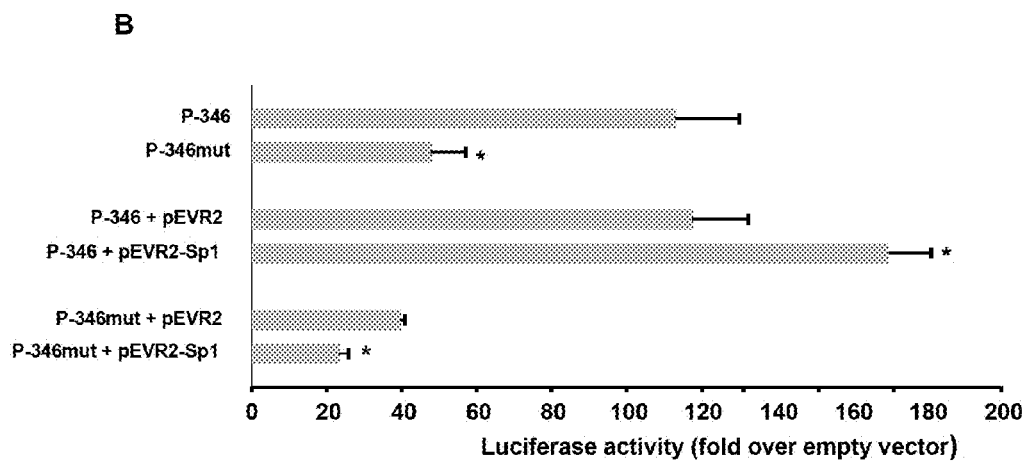
FIG. 4B shows: the site-directed mutagenesis of the putative Sp1-binding site on the FPR2/ALX promoter activity; the luciferase activity of P-346 vs P-346mut (*, P=0.01) and the impact of Sp1 overexpression on P-346 (*, P=0.026) and on P-346mut promoter activity. Luciferase activity was measured 48 h post transfection of MDA-MB231 cells with P-346 together with the pEVR2 expression plasmid containing or not Sp1. Results are expressed as mean±S.D. of n=3 carried out with duplicate determinations.

In order to assess Sp1 binding to the FPR2/ALX promoter, we immunoprecipitated sheared chromatin with an Sp1-specific antibody and then carried out PCR amplification of a 120 bp sequence (−345 to −225 from the TSS) that included the putative Sp1 binding site. As shown in FIG. 4A, we obtained a specific PCR product of the expected size, confirming SP1 binding to the predicted site in the FPR2/ALX promoter. Next, we examined the transactivation capacity of Sp1. To this end, we carried out site-directed mutagenesis of the SP1 binding site (GG at −238 bp from the TSS was replaced with TT) (FIG. 4B)

SEQ. ID. NO. 33
GGCTGAAACTCTTCCCACTTCAGTAATTGTTTCTTTCATTTTCATGAAACTCTGAAGAAGGA

AGGGCTGGACATTCAGATTCCTTGACCCTTGACATTT

SEQ. ID. NO. 34
GGCTGAAACTCTTCCCACTTCAGTAATTGTTTCTTTCATTTTCATGAAACTCTGAAGAAGGA

AGGGCTTTTACATTCAGATTCCTTGACCCTTGACATTT and cloned the mutated sequence into a reporter plasmid (mut SP1), which was transfected into MDA-MB 231 cells. This mutation significantly reduced (P=0.01) promoter activity of wt P-346 (FIG. 4C). To obtain further evidence of the role played by Sp1 in the regulation of FPR2/ALX activity, we co-transfected an expression plasmid encoding for human Sp1 (pEVR2/Sp1) and P-346 into MDA-MB231 cells and determined the reporter gene activity. As shown in FIG. 4C, the Sp1-expressing plasmid enhanced significantly the promoter activity of P-346 (P=0.026), but it did not increase the activity of mutated P-346.

Example 5

Regulatory Mechanisms of the FPR2/ALX Promoter

Figure 5:
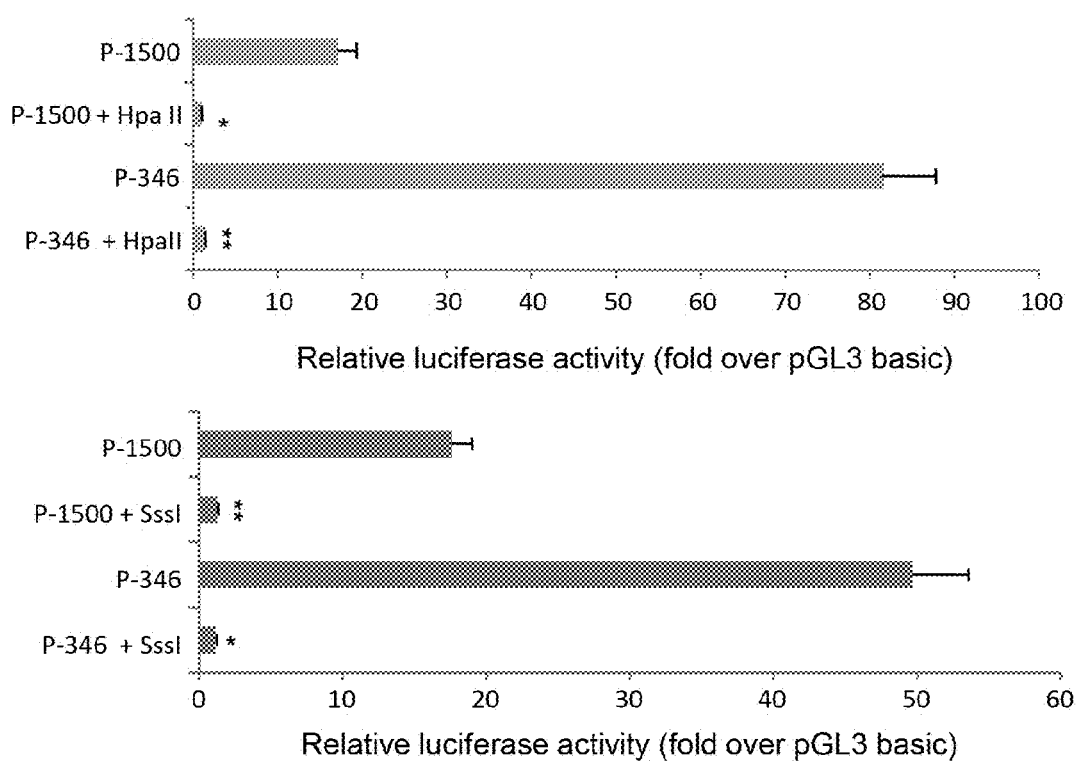
FIG. 5. Epigenetic regulation of FPR2/ALX promoter activity. Reporter gene assays with P-1500 and P-346 methylated in vitro and transfected into MDA-MB231. Luciferase activity was determined 24 h post-transfection. Upper panel. Results with HpaII methylase (mean±S.D. of at least three independent experiments with duplicates (*, P=0.0025; **, P=0.0019 vs unmethylated constructs). Lower panel. Data from experiments with SssI methylase (mean±S.D. of two independent experiments with duplicates (*, P=0.00009; **, P=0.00006 vs unmethylated constructs).
Figure 6:
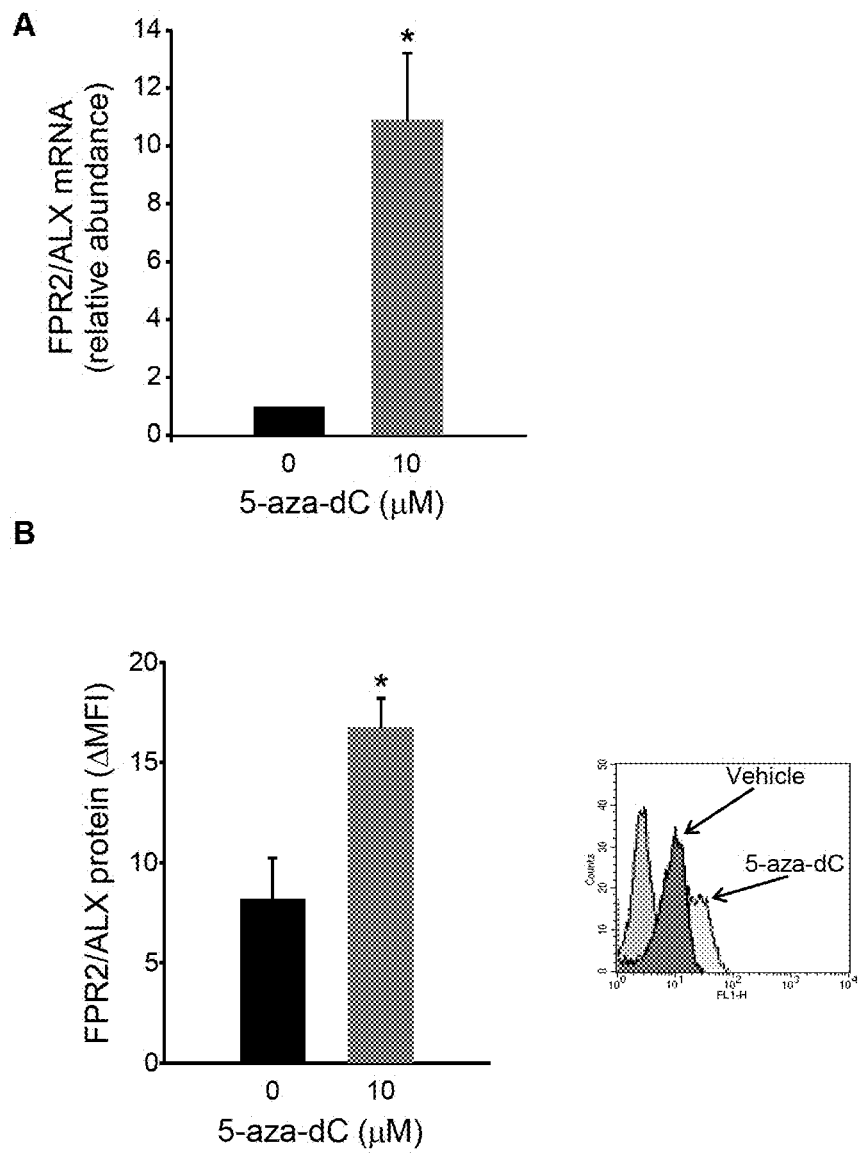
FIG. 6. Regulation of FPR2/ALX mRNA and protein expression by 5-aza-dC. MDA-MB231 cells were treated with 10 µM 5-Aza-dC and FPR2/ALX expression was determined using real time PCR (A) and flow cytometry (B). In this latter, results are expressed as Δ mean fluorescence intensity (MFI) by subtracting the MFI of IgG stained cells from the MR of anti-FPR2/ALX-stained cells (Mean±SD, n=3; *, P=0.0046 for protein and P=0.0018 for mRNA vs untreated cells). Representative cytometric plot of FPR2/ALX expression in MDA-MB231 cells untreated or treated with 10 µM 5-aza-dC or cells incubated with antibody-matched control.

We next investigated epigenetic regulation of FPR2/ALX promoter activity. Although in silico analysis did not reveal CpG motifs within the P-1500, a number of potential targets for HpaII (CCGG motifs) and SssI (CpG dinucleotides) methylases was found. Therefore P-1500 and P-346 were methylated in vitro. To this end, Four micrograms of plasmid DNA were incubated (16 h, 37° C.) with 0.8 units/μg of the methylases HpaII (Fermentas, Opelstrasse Germany), SssI (NEB, Ipswich, Mass., USA) and HhaI in buffer containing 10 mM Tris-HCl, 50 mM NaCl, 10 mM MgCl2, 1 mM DTT, and 800 μM of S-adenosylmethionine. Methylation was confirmed by plasmid digestion with the restriction enzymes HpaII, BstUI and HhaI. The methylated plasmids were purified by QIAquick PCR Purification Kit (Qiagen, Milan, Italy) and transfected into MDA-MB231 as described above. Cells were transfected with 2 μg of P-346 and were used equimolar amounts of other plasmids. Luciferase activity was measured as described above. HpaII and SssI methylated P-1500 as well as P-346 in vitro and suppressed promoter activity (FIG. 5). In contrast, only one predicted target for the HhaI methylase (GCGC motif) was found in P-1500 and none in P-346. Indeed, HhaI did not give appreciable methylation and promoter activity inhibition (results not shown). In accordance with data in FIG. 5, the de-methylating agent 5-aza-dC increased both FPR2/ALX mRNA (by ~10 fold) and protein (~3 fold) expression in MDA-MB231 cells (FIGS. 6A and B). For 5-aza-2'-deoxycytidine (5-aza-dC) treatment, cells were seeded in 100 mm tissue culture dish and maintained for 96 h. 5-aza-dC was added after 24 h, and cells were incubated for 72 h with culture medium replaced every 24 h.

Figure 7:
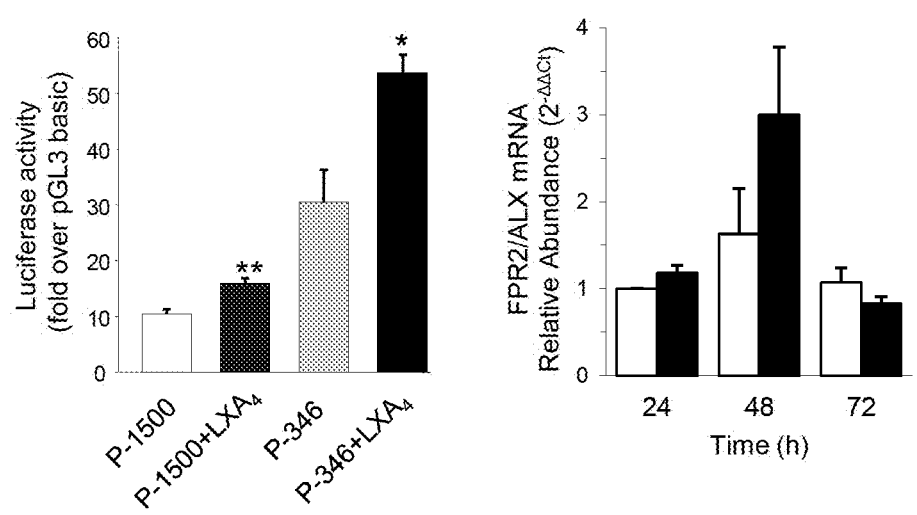
FIG. 7 shows LXA4 up-regulation of FPR2/ALX promoter activity and FPR2/ALX mRNA level. Left panel. MDA-MB231 cells were transfected with P-1500 or P-346. Twenty four hours post-transfection, cells were exposed to ethanol vehicle or 10 nM LXA4 for additional 24 h. Bars depict mean±S.D. of n=4 carried out with duplicates. *, P= 0.018; **, P=0.0076 vs vehicle-treated cells. Right panel. MDA-MB231 cells were exposed to LXA4 (10 nM) for the indicated time. FPR2/ALX mRNA was quantitated by real-time PCR. Bars show mean±S.D. of n=3. *, P=0.05.

Expression of GPCRs can be upregulated by the relative agonists. For example, LTB4 increases mRNA and protein expression of the LTB4 receptor 1 (BLT1) in endothelial cells (Qiu, H., A. S. Johansson, M. Sjöström, M. Wan, O, Schröder, J. Palmblad, and J. Z. Haeggström. 2006. Differential induction of BLT receptor expression on human endothelial cells by lipopolysaccharide, cytokines, and leukotriene B4. Proc Natl Acad Sci USA 103:6913-6918). Moreover, FPR2/ALX cellular expression can be enhanced by corticosteroids (Sawmynaden, P., and M. Perretti. 2006. Glucocorticoid upregulation of the annexin-A1 receptor in leukocytes. Biochem Biophys Res Commun 349:1351-1355) and cytokines (Gronert, K., A. Gewirtz, J. L. Madara, and C. N. Serhan. 1998. Identification of a human enterocyte lipoxin A4 receptor that is regulated by interleukin (IL)-13 and interferon gamma and inhibits tumor necrosis factor alpha-induced IL-8 release. J Exp Med 187:1285-1294). Therefore, we examined the impact of LXA$_4$ (primary FPR2/ALX agonist) as well as of corticosteroids and cytokines on the activity of the FPR2/ALX promoter. To this end, we transfected MDA-MB231 cells with P-1500 and P-346 for 24 hours before exposure to LXA4 (10 nM), dexamethasone (1 μM), gamma interferon (IFN-γ) (5-100 nM), lipopolysaccharide (LPS) (500 nM). Only LXA4 significantly enhanced luciferase activity of p-1500 and P-346 and enhanced FPR2/ALX mRNA levels (FIG. 7), whereas the other agents did not give appreciable changes (results not shown).

Example 6

Identification of a Single Nucleotide Polymorphism in the FPR2/ALX Promoter

In light of the emerging pathophysiological relevance of FPR2/ALX in human disease, the inventors asked whether genetic variants of the identified promoter sequence could be found in humans. Therefore, the core promoter in DNA from 100 healthy individuals and 100 patients with history of acute cardiovascular events was sequenced, in consideration of the documented protective action of the LXA4/LXA4 receptor in the vascular district (Chiang, N., C. N. Serhan, S. E. Dahlen, J. M. Drazen, D. W. Hay, G. E. Rovati, T. Shimizu, T. Yokomizo, and C. Brink. 2006. The lipoxin receptor ALX: potent ligand-specific and stereoselective actions in vivo. Pharmacol Rev 58:463-487). The analysis of polymorphisms was carried out by means of the following protocol: genomic DNA of 132 patients with acute coronary ischemia available from the Monzino Cardiologic Institute (Milan, Italy) and from 100 healthy subjects recruited at the Functional Genomic Unit of the Center of Excellence on Aging (Chieti, Italy) was sequenced following PCR amplification of the FPR2/ALX 5' flanking region. Two primers, For 346 bp and Rev 346 bp (Table 1), complementary to P-346 were used to amplify a portion of DNA starting −306 bp upstream of the identified TSS (+1). PCR products were purified and sequenced using an ABI PRISM 3100 Genetic Analyzer. Each PCR product was sequenced both in the forward and in the reverse strand. Detected mutations were confirmed by repeating the sequencing on a new PCR product. We found no mutations in healthy subjects. On the contrary, one patient with pregress acute coronary ischemia and affected by metabolic syndrome was heterozygous for a single base mutation (A/G) at −220 bp upstream the TSS.

To evaluate the impact of this genetic variant on the promoter activity, the wild type core promoter was mutated in vitro introducing the A/G single nucleotide polymorphism (SNP).

(SEQ ID. NO: 35)
GGCTGAAACTCTTCCCACTTCAGTAATTGTTTCTTTCATTTTCATGAAACTCTGAAGAAGGA

AGGGCTGGACATTCAGATTCCTTGACCCTTGACATTTG.

(SEQ ID. NO: 36)
GGCTGAAACTCTTCCCACTTCAGTAATTGTTTCTTTCATTTTCATGAAACTCTGAAGAAGGA

AGGGCTGGACATTCAGATTCCTTGGCCCTTGACATTTG.

Remarkably, the mutated construct (P-346 pt mut) showed ~35% reduction in promoter activity compared to the wild type P-346 when transfected into MDA-MB231 cells.

Figure 8:
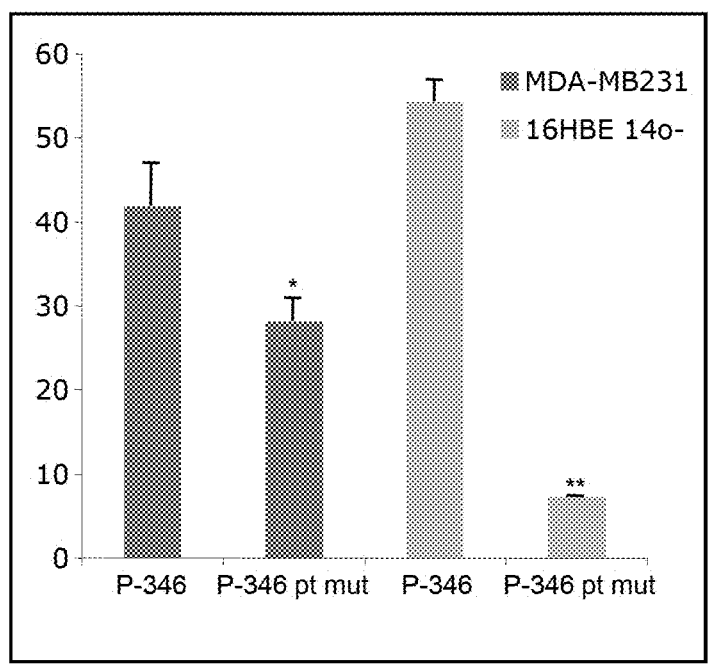
FIG. 8 shows the Identification of one SNP in the FPR2/ALX core promoter. Reduced transcriptional activity of P-346 pt mut in MDA-MB231 and 16 HBE cells. Luciferase reporter activity was assessed 48 h after transfection. Results depict mean±S.D. from n=3, with duplicates (*P=0.001; **, P=0.00029 vs wild type).
Figure 9:
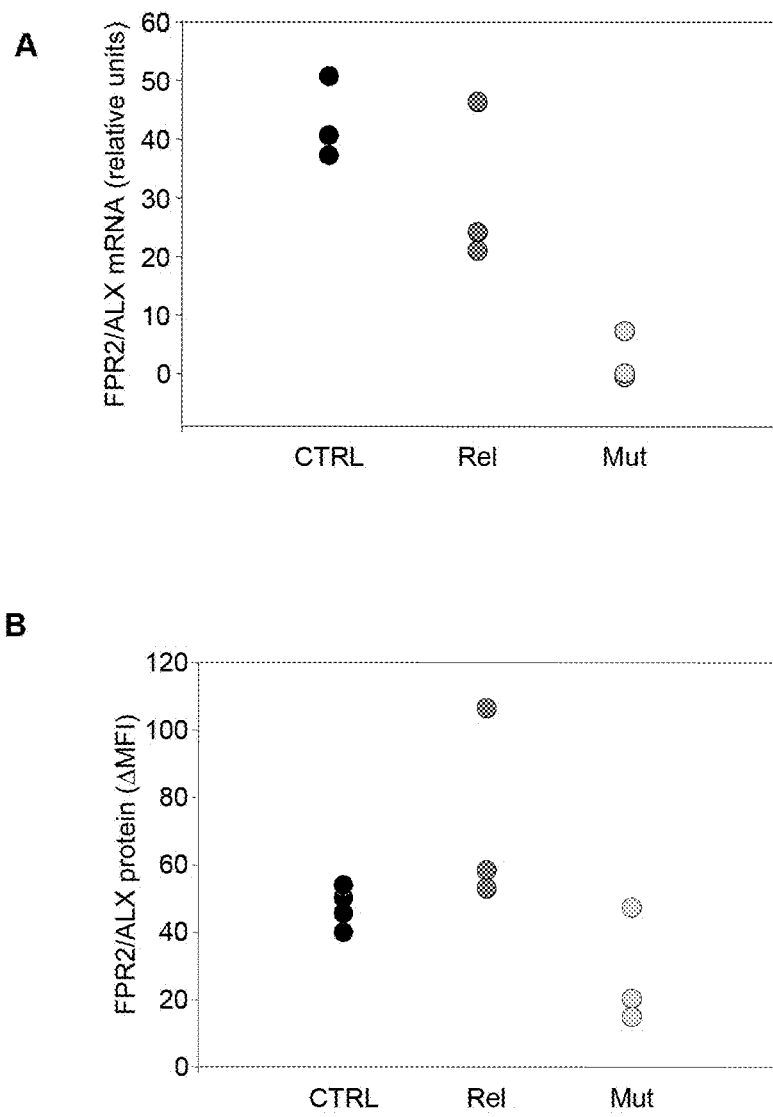
FIG. 9. Carriers of the −220 AIG SNP have reduced FPR2/ALX expression in PMN. (a) Real time PCR analysis of FPR2/ALX mRNA from PMN isolated from the proband and his two daughters (Mut), from the proband relatives not carrying the mutation (Rel) and from age- and sex-matched healthy volunteers (CTRL). (b) Flow cytometric analysis of FPR2/ALX protein expression on PMN from the same subjects.

This reduction reached ~90% when the mutant was transfected into the human airway cell line 16HBE14o- (FIG. 8). The cells were grown to confluence in Minimum Essential Medium Eagle (MEM, PAA) with Earle's balanced salt solution, supplemented with 10% FBS vol/vol and 100 U/ml P/S on 100 mm plates coated with fibronectin and collagen.

Gene sequence analysis of DNA from the proband relatives revealed that his two daughters both carried the A/G 220 variant in heterozygosis, whereas two brothers and one sister expressed the wt allele. The parents could not be genotyped because were deceased. Therefore FPR2/ALX mRNA and protein expression in PMN from these individuals as well from age and sex-matched normal individuals was evaluated. Blood samples were collected into citric acid-citrate-dextrose (Becton Dickinson, Franklin Lakes, N.J., USA) for leukocyte isolation and RNA extraction and into a citrate containing Vacutainer® tube (1/10 vol sodium citrate 0.129 mol/L, Becton Dickinson) for whole blood flow cytometry analysis. Blood leukocytes were separated by Ficoll-Histopaque/Dextran sedimentation.

To carry out the quantitative real-time PCR, total RNA was isolated from MDA-MB231 or circulating PMN using Rneasy Plus Mini Kit (Qiagen) and reverse transcribed using M-MLV Reverse Transcriptase (Sigma-Aldrich). Quantitative PCR was performed with an ABI PRISM 7900 HT real time PCR thermal cycler. Duplicates were set up for each sample and the expression of FPR2/ALX mRNA was quantified by the comparative ΔΔCT method (Livak and Schmittgen, 2001), using FPR2/ALX assay on demand Applied Biosystem, (Hs 00265954_m1). Ct values were normalized using TaqMan™ GAPDH assay on demand by Applied Biosystem, (Hs 99999905_1) as housekeeping gene.

For the evaluation of FPR2/ALX protein expression in PMN, cells were fixed with 2% paraformaldehyde for 10 minutes at 4° C. and permeabilized with BD Permeabilizing Solution 2 (Becton Dickinson, Franklin Lakes, N.J., USA) for 10 minutes at room temperature. For each staining $5 \times 10^5$ cells were incubated with anti-FPR2/ALX (Genovac GmbH, Freiburg, Germany) in PBS containing 0.5% bovine serum albumin (BSA, Sigma-Aldrich) (30 minutes, 4° C.), followed by fluorochrome-conjugated secondary antibody (Sigma-Aldrich) in the same buffer (30 minutes, 4° C.). Secondary antibody-matched controls were used to assess unspecific fluorescence. Samples were analyzed using a FACSCalibur flowcytometer (Becton Dickinson) and data were analyzed using CELLQuest software (Becton Dickinson). We observed that the three subjects heterozygous for the A/G 220 variant had lower levels of FPR2/ALX mRNA and protein in blood PMN compared to their wt relatives, who showed expression levels comparable to those observed in healthy individuals, age- and sex-matched.

The invention claimed is:

1. A method for predicting responsiveness of a subject at risk of having or developing an inflammatory disease and/or an inflammatory event to a drug stimulating activity of an FPR2/ALX gene promoter comprising:
   a) adding an active ingredient to two screening systems, a first screening system expressing a wild type FPR2/ALX promoter comprising SEQ ID NO: 3 and a second screening system expressing a FPR2/ALX promoter comprising a SNP, the sequence consisting of SEQ ID NO: 6, in parallel;
   b) detecting responsiveness of wild type FPR2/ALX promoter and the FPR2/ALX promoter consisting of SEQ ID NO: 6 to said active ingredient; and
   c) comparing expression of a reporter gene in a cell line expressing the wild type FPR2/ALX promoter of SEQ ID NO: 3 with expression of a reporter gene in a cell line expressing the FPR2/ALX promoter consisting of SEQ ID NO: 6;
   d) wherein the responsiveness of a subject to the active ingredient is based on the responsiveness of the wild type FPR2/ALX promoter having SEQ ID NO: 3 and the FPR2/ALX promoter consisting of SEQ ID NO: 6 to the active ingredient.

2. A method for identifying active ingredients for use in treating inflammatory diseases, said method for identifying active ingredients comprising adding an active ingredient to a screening system comprising:
   a nucleotide sequence of a core promoter of a FPR2/ALX gene comprising SEQ ID NO: 3 or consisting of SEQ ID NO: 6,
   an expression vector comprising said nucleotide sequence and a reporter gene, and
   a cell line expressing an endogenous FPR2/ALX gene; and
   detecting activity of said active ingredient on expression of the reporter gene.

3. The method according to claim 2, wherein the nucleotide sequence of the core promoter of the FPR2/ALX gene comprises wild type form of SEQ ID NO: 3, the expression vector comprises SEQ ID NO: 3 and a reporter gene, and the cell line expressing the endogenous FPR2/ALX gene is MDA-MB231.

* * * * *

SEQUENCE LISTING

<160> NUMBER OF SEQ ID NOS: 37

<210> SEQ ID NO 1
<211> LENGTH: 2639
<212> TYPE: DNA
<213> ORGANISM: Homo sapiens

<400> SEQUENCE: 1

```
aggaccagga acaacctatt tgcaaagttg gcgcaaacat tcctgcctga caggaccatg      60
gacacaggtt gtagagatag agatggctct ggctgtgcat tcagcagatt ctgtagatag     120
aattaatagg acttggatgg gattgtggtg agagaaagtg aaatgaaaga taagttctag     180
tttggaagtt ttaacaactg aatgtttaaa ctcaaataga cacaaaatat tggaagagtg     240
gcaggtttgg gaggatgaga caatcaactg tttggttgag ccacgttagg tttgaaatgt     300
ctacgggact cccgtgggga gaggttatat cagactggag caccagagag aggccaaggc     360
tgatagttta gatgaaaaga gagcatgata ttttaagccc tgagactgga taatatcacc     420
tatagaaaga ctatatagag ataagagagg tggggaacaa gtaaaagctg cgggacactc     480
ctaaatttag agtcaaattt agagcagaaa atactagcaa aggggactga aaagcggtgg     540
ccaattgagc ttcaaatgca agtgaaagtg tgttgtgtgt acatttatca tctcatggca     600
caggaaaaac gtgatttaag gagaaggaag cgatccaatg ggaagaagag atccaatgga     660
```

```
tcctctatca cgaagatatt gagataagaa ccaatatgga tttgcaccca ctgcatttgc      720
agccttgagg tcataagcat cctcaggaaa atgcaccagg tgctgctggc aagatggaaa      780
ccaacttctc cactcctctg aatgaatatg aagaagtgtc ctatgagtct gctggctaca      840
ctgttctgcg gatcctccca ttggtggtgc ttggggtcac ctttgtcctc ggggtcctgg      900
gcaatgggct tgtgatctgg gtggctggat ccggatgac acgcacagtc accaccatct       960
gttacctgaa cctggccctg gctgactttt ctttcacggc cacattacca ttcctcattg     1020
tctccatggc catgggagaa aaatggcctt ttggctggtt cctgtgtaag ttaattcaca     1080
tcgtggtgga catcaacctc tttggaagtg tcttcttgat tggtttcatt gcactggacc     1140
gctgcatttg tgtcctgcat ccagtctggg cccagaacca ccgcactgtg agtctggcca     1200
tgaaggtgat cgtcggacct tggattcttg ctctagtcct taccttgcca gttttcctct     1260
ttttgactac agtaactatt ccaaatgggg acacatactg tactttcaac tttgcatcct     1320
ggggtggcac ccctgaggag aggctgaagg tggccattac catgctgaca gccagaggga     1380
ttatccggtt tgtcattggc tttagcttgc cgatgtccat tgttgccatc tgctatgggc     1440
tcattgcagc caagatccac aaaaagggca tgattaaatc cagccgtccc ttacgggtcc     1500
tcactgctgt ggtggcttct ttcttcatct gttggtttcc ctttcaactg gttgcccttc     1560
tgggcaccgt ctggctcaaa gagatgttgt tctatggcaa gtacaaaatc attgacatcc     1620
tggttaaccc aacgagctcc ctggccttct tcaacagctg cctcaacccc atgctttacg     1680
tctttgtggg ccaagacttc cgagagagac tgatccactc cctgcccacc agtctggaga     1740
gggccctgtc tgaggactca gccccaacta atgcacggc tgccaattct gcttcacctc      1800
ctgcagagac tgagttacag gcaatgtgag gatggggtca gggatatttt gagttctgtt     1860
catcctaccc taatgccagt tccagcttca tctaccttg agtcatattg aggcattcaa      1920
ggatgcacag ctcaagtatt tattcaggaa aaatgctttt gtgtccctga tttggggcta     1980
agaaatagac agtcaggcta ctaaaatatt agtgttattt tttgtttttt gacttctgcc     2040 tatacccctgg ggtaagtgga gttgggaaat acaagaagag aaagaccagt ggggatttgt    2100
aagacttaga tgagatagcg cataataagg ggaagacttt aaagtataaa gtaaaatgtt     2160
tgctgtaggt ttttttatagc tattaaaaaa aatcagatta tggaagtttt cttctatttt    2220
tagtttgcta agagttttct gtttcttttt cttacatcat gagtggactt tgcatttat     2280 caaatgcatt ttctacatgt attaagatgg tcatattatt cttcttcttt tatgtaaatc     2340
attataaata atgttcatta agttctgaat gttaaactac tcttgaattc ctggaataaa     2400
ccacacttag tcctgatgta ctttaaatat ttatatctca caggagttgg ttagaatttc     2460
tgtgtttatg tttatatact gttatttcac tttttctact atccttgcta agttttcata    2520
gaaaataagg aacaaagaga aacttgtaat ggtctctgaa aaggaattga gaagtaattc     2580
ctctgattct gttttctggt gttatatctt tattaaatat tcagaaaaat tcaccagtg      2639
```

<210> SEQ ID NO 2
<211> LENGTH: 2259
<212> TYPE: DNA
<213> ORGANISM: Homo sapiens

<400> SEQUENCE: 2

```
tcatatttgg gcttgattgc gtggctgaaa ctcttcccac ttcagtaatt gtttctttca       60
ttttcatgaa actctgaaga aggaagggct ggacattcag attccttgac ccttgacatt      120
tggaagcatg aactccagtc tctcacagaa ggctagaggt gaaggaacat tcagacacat      180
```

```
tggtttctaa gaagagtccg ctgacaacat acccaaggtg tcttctgaaa attataagaa      240
atcctgagtt tctgttaggg gattggctcc agctccattg tccctccccc atcattcagt      300
agtctccgcg aaagccctta gagccggtgt tgctccacag gaagccaaga agcacacagg      360
aaaaggagct tagctgctgg tgctgctggc aagatggaaa ccaacttctc cactcctctg      420
aatgaatatg aagaagtgtc ctatgagtct gctggctaca ctgttctgcg gatcctccca      480
ttggtggtgc ttggggtcac ctttgtcctc ggggtcctgg gcaatgggct tgtgatctgg      540
gtggctggat tccggatgac acgcacagtc accaccatct gttacctgaa cctggccctg      600
gctgactttt ctttcacggc cacattacca ttcctcattg tctccatggc catgggagaa      660
aaatggcctt ttggctggtt cctgtgtaag ttaattcaca tcgtggtgga catcaacctc      720
tttggaagtg tcttcttgat tggtttcatt gcactggacc gctgcatttg tgtcctgcat      780
ccagtctggg cccagaacca ccgcactgtg agtctggcca tgaaggtgat cgtcggacct      840
tggattcttg ctctagtcct taccttgcca gttttcctct ttttgactac agtaactatt      900
ccaaatgggg acacatactg tactttcaac tttgcatcct ggggtggcac ccctgaggag      960
aggctgaagg tggccattac catgctgaca gccagaggga ttatccggtt tgtcattggc     1020
tttagcttgc cgatgtccat tgttgccatc tgctatgggc tcattgcagc caagatccac     1080
aaaaagggca tgattaaatc cagccgtccc ttacgggtcc tcactgctgt ggtgcttct     1140 ttcttcatct gttggtttcc ctttcaactg gttgcccttc tgggcaccgt ctggctcaaa     1200
gagatgttgt tctatggcaa gtacaaaatc attgacatcc tggttaaccc aacgagctcc     1260
ctggccttct tcaacagctg cctcaacccc atgctttacg tctttgtggg ccaagacttc     1320
cgagagagac tgatccactc cctgcccacc agtctggaga gggccctgtc tgaggactca     1380
gccccaacta atgacacggc tgccaattct gcttcacctc ctgcagagac tgagttacag     1440
gcaatgtgag gatggggtca gggatatttt gagttctgtt catcctaccc taatgccagt     1500
tccagcttca tctacccttg agtcatattg aggcattcaa ggatgcacag ctcaagtatt     1560
tattcaggaa aaatgctttt gtgtccctga tttggggcta agaaatagac agtcaggcta     1620
ctaaaatatt agtgttattt tttgtttttt gacttctgcc tataccctgg ggtaagtgga     1680
gttgggaaat acaagaagag aaagaccagt ggggatttgt aagacttaga tgagatagcg     1740
cataataagg ggaagacttt aaagtataaa gtaaaatgtt tgctgtaggt ttttatagc     1800 tattaaaaaa aatcagatta tggaagtttt cttctatttt tagtttgcta agagttttct     1860
gtttcttttt cttacatcat gagtggactt tgcattttat caaatgcatt ttctacatgt     1920
attaagatgg tcatattatt cttcttcttt tatgtaaatc attataaata atgttcatta     1980
agttctgaat gttaaactac tcttgaattc ctggaataaa ccacacttag tcctgatgta     2040
ctttaaatat ttatatctca caggagttgg ttagaatttc tgtgtttatg tttatatact     2100
gttatttcac tttttctact atccttgcta agttttcata gaaaataagg aacaaagaga     2160
aacttgtaat ggtctctgaa aaggaattga gaagtaattc ctctgattct gtttttctggt     2220 gttatatctt tattaaatat tcagaaaaat tcaccagtg                             2259
```

<210> SEQ ID NO 3
<211> LENGTH: 346
<212> TYPE: DNA
<213> ORGANISM: Homo sapiens

<400> SEQUENCE: 3

```
ggctgaaact cttcccactt cagtaattgt ttctttcatt ttcatgaaac tctgaagaag      60
gaagggctgg acattcagat tccttgaccc ttgacatttg gaagcatgaa ctccagtctc     120
tcacagaagg ctagaggtga aggaacattc agacacattg gtttctaaga agagtccgct     180
gacaacatac ccaaggtgtc ttctgaaaat tataagaaat cctgagtttc tgttagggga     240
ttggctccag ctccattgtc cctcccccat cattcagtag tctccgcgaa agcccttaga     300
gccggtgttg ctccacagga agccaagaag cacacaggaa aaggag                    346

<210> SEQ ID NO 4
<211> LENGTH: 1489
<212> TYPE: DNA
<213> ORGANISM: Homo sapiens

<400> SEQUENCE: 4
taatgcttat tgctgtctgc cttatcatct atgctctggt aaacaaaagt aacctgcttt      60
tttgtgaccc ctttcgtggg tattttttact cccctctgac aagaatgcat tattttttct    120
cctttatctg agtctttaag actcagccta catgttccct cctccggata ttgactctag    180
atccgtgaat ctgagttagt ggttcctttt agaggacctc acaaggagcc aggcatctgt    240
ctatcactac gtgcccccac cctattgtaa ctaagcactg cattctcacc tctctattca    300
ggtggtccgc agagcccatg tctgattgat ctctatgtct ccagcagcca gcaaggaagc    360
acctctttag agacctgcac ctatacaata cctaccacct tttatttctc gatatgtgaa    420
ctccattgag aacaaacgag taaatgtagg taatgtgcct tcttcttttc ttttcttttc    480
tttttttttt tagatggagt ctcgctctgt gcccaggct ggagtttagt ggcacaatct      540
cggctcactg taacctccgc ctcccaggtt caagcgattc tgccgcctca gcctaccaag    600
tagttgggat tacaggtgcc caccaccacg cccagctaat ttttttttgta ttttttagtag   660 aggtggggtt tcatgatgtt ggctaggatg gttttcaact cctgacctca agtgatccac    720
ccacctcggc ctcccaaagt gctaggatta caggtgtgag ccacagcgcc agcagtaa     780 tgtgccttct taagttctgt gagccattct aacaaattat cagaacagag gaaggggtta   840
taaacatccc cccacccccg atttatagcc agtcagtcag aagtacaggt ggccacctgg   900
gacttggatt ggtgtctgaa gtgaggacag ttttgggaga gtgagcccctt aacttgtgg   960 gatctgacac taactccagg tagacagcgt cggagctgaa ttgaattgtg agatacccag  1020
tggtgtcccc agagaactgg agaattgctt gatatggaaa agacccacac atttgatgcc  1080
agaagtactg cataagtcga gaattgagtt tgacttaatc atcatatttg ggcttgattg  1140
cgtggctgaa actcttccca cttcagtaat tgtttctttc attttcatga aactctgaag  1200
aaggaagggc tggacattca gattccttga cccttgacat ttggaagcat gaactccagt  1260
ctctcacaga aggctagagg tgaaggaaca ttcagacaca ttggtttcta agaagagtcc  1320
gctgacaaca tacccaaggt gtcttctgaa aattataaga aatcctgagt ttctgttagg  1380
ggattggctc cagctccatt gtccctcccc catcattcag tagtctccgc gaaagccctt  1440
agagccggtg ttgctccaca ggaagccaag aagcacacag gaaaaggag              1489

<210> SEQ ID NO 5
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

-continued

```
<400> SEQUENCE: 5
gcgtggctga aactcttccc acttcagtaa ttgtttcttt cattttcatg aaactctgaa      60
gaaggaaggg ctttacattc agattccttg acccttgaca tttggaagca tgaactccag     120
tctctcacag aaggctagag gtgaaggaac attcagacac attggtttct aagaagagtc     180
cgctgacaac atacccaagg tgtcttctga aaattataag aaatcctgag tttctgttag     240
gggattggct ccagctccat tgtccctccc ccatcattca gtagtctccg cgaaagccct     300
tagagccggt gttgctccac aggaagccaa gaagcacaca ggaaaaggag cttagctgct     360
ggtaag                                                                366

<210> SEQ ID NO 6
<211> LENGTH: 346
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
ggctgaaact cttcccactt cagtaattgt ttctttcatt ttcatgaaac tctgaagaag      60
gaagggctgg acattcagat tccttgaccc ttgacgtttg gaagcatgaa ctccagtctc     120
tcacagaagg ctagaggtga aggaacattc agacacattg gtttctaaga gagtccgct     180 gacaacatac caaggtgtc ttctgaaaat tataagaaat cctgagtttc tgttagggga     240
ttggctccag ctccattgtc cctcccccat cattcagtag tctccgcgaa agcccttaga     300
gccggtgttg ctccacagga agccaagaag cacacaggaa aaggag                    346

<210> SEQ ID NO 7
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cgactggagc acgaggacac tga                                              23

<210> SEQ ID NO 8
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
ggacactgac atggactgaa ggagta                                           26

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 9
ggttcaggta acagatggtg gtgac                                    25

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
agatcacaag cccattgccc agg                                      23

<210> SEQ ID NO 11
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ttaatgctta ttgctgtctg cc                                       22

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12 ctcctttttcc tgtgtgcttc                                         20

<210> SEQ ID NO 13
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
ggggtacctt aatgcttatt gctgtctgcc                               30

<210> SEQ ID NO 14
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ccgctcgacc tccttttcct gtgtgcttc                                29

<210> SEQ ID NO 15
<211> LENGTH: 22
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 15
ttaatgctta ttgctgtctg cc                                              22

<210> SEQ ID NO 16
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
agaatggctc acagaactta ag                                              22

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
aacaaattat cagaacagag g                                               21

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
actcaattct cgacttatgc                                                 20

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ggctgaaact cttcccac                                                   18

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ccgactttga gaagggtg                                                   18
```

<210> SEQ ID NO 21
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 21
agattccttg acccttgac                                                  19

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 22
ttctaagaag agtccgctg                                                  19

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 23
gagtttctgt tagggattg                                                  19

<210> SEQ ID NO 24
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 24
agtagtctcc gcgaaagcc                                                  19

<210> SEQ ID NO 25
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 25
ctctgaagaa ggaagttctg gacattcaga tt                                   32

<210> SEQ ID NO 26
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

```
<400> SEQUENCE: 26
aatctgaatg tccagaactt ccttcttcag ag                                32

<210> SEQ ID NO 27
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gattccttga cccttgacgt ttggaagcat gaactcc                           37

<210> SEQ ID NO 28
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ggagttcatg cttccaaacg ycaagggtca aggaatc                           37

<210> SEQ ID NO 29
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
gggcttgatt gcgtggc                                                 17

<210> SEQ ID NO 30
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tcagacaggg ccctctc                                                 17

<210> SEQ ID NO 31
<211> LENGTH: 210
<212> TYPE: DNA
<213> ORGANISM: Homo sapiens

<400> SEQUENCE: 31
gttgctccac aggaagccaa gaagcacaca ggaaaaggag cttagctgct ggtgctgctg    60
gcaagatgga aaccaacttc tccactcctc tgaatgaata tgaagaagtg tcctatgagt   120
ctgctggcta cactgttctg cggatcctcc cattggtggt gcttggggtc acctttgtcc   180
tcggggtcct gggcaatggg cttgtgatct                                   210

<210> SEQ ID NO 32
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gagactggag ttcatgcttc                                              20

<210> SEQ ID NO 33
<211> LENGTH: 99
<212> TYPE: DNA
<213> ORGANISM: Homo sapiens

<400> SEQUENCE: 33 ggctgaaaact cttcccactt cagtaattgt ttctttcatt ttcatgaaac tctgaagaag   60
gaagggctgg acattcagat tccttgaccc ttgacattt                          99

<210> SEQ ID NO 34
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34 ggctgaaaact cttcccactt cagtaattgt ttctttcatt ttcatgaaac tctgaagaag   60
gaagggcttt acattcagat tccttgaccc ttgacattt                          99

<210> SEQ ID NO 35
<211> LENGTH: 100
<212> TYPE: DNA
<213> ORGANISM: Homo sapiens

<400> SEQUENCE: 35 ggctgaaaact cttcccactt cagtaattgt ttctttcatt ttcatgaaac tctgaagaag   60
gaagggctgg acattcagat tccttgaccc ttgacatttg                        100

<210> SEQ ID NO 36
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36 ggctgaaaact cttcccactt cagtaattgt ttctttcatt ttcatgaaac tctgaagaag   60
gaagggctgg acattcagat tccttggccc ttgacatttg                        100

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 37
gctgaaactc ttcccacttc                                                  20
```